US010376159B2

(12) United States Patent
Morris et al.

(10) Patent No.: US 10,376,159 B2

(45) Date of Patent: Aug. 13, 2019

(54) EXERCISE TRIGGERED CARDIOVASCULAR PRESSURE MEASUREMENT

(71) Applicant: Medtronic, Inc., Minneapolis, MN (US)

(72) Inventors: Mary M. Morris, Shoreview, MN (US); Ruth N. Klepfer, St. Louis Park, MN (US); Karen J. Kleckner, New Brighton, MN (US); Joel R. Lauer, Clearwater, MN (US)

(73) Assignee: Medtronic, Inc., Minneapolis, MN (US)

(*) Notice: Subject to any disclaimer, the term of this patent is extended or adjusted under 35 U.S.C. 154(b) by 269 days.

(21) Appl. No.: 15/384,709

(22) Filed: Dec. 20, 2016

(65) Prior Publication Data

US 2018/0168463 A1 Jun. 21, 2018

(51) Int. Cl.

| | |
|---|---|
| ***A61B 5/0205*** | (2006.01) |
| ***A61B 5/0215*** | (2006.01) |
| ***A61B 5/00*** | (2006.01) |
| ***A61B 5/11*** | (2006.01) |
| ***A61N 1/365*** | (2006.01) |

(Continued)

(52) U.S. Cl.

CPC ........ *A61B 5/02055* (2013.01); *A61B 5/0024* (2013.01); *A61B 5/0031* (2013.01); *A61B 5/0215* (2013.01); *A61B 5/1118* (2013.01); *A61B 5/4836* (2013.01); *A61B 5/686* (2013.01); *A61B 5/7221* (2013.01); *A61N 1/365* (2013.01); *A61N 1/3956* (2013.01); *A61N 1/3987* (2013.01); *G16H 20/30* (2018.01); *G16H 40/63* (2018.01); *A61B 5/024* (2013.01); *A61B 5/0816* (2013.01); *A61B 5/6876* (2013.01); *A61B 2562/0219* (2013.01)

(58) Field of Classification Search

CPC ............................ A61B 5/1118; A61B 5/0024

See application file for complete search history.

(56) References Cited

U.S. PATENT DOCUMENTS 5,117,824 A 6/1992 Keimel et al.
5,331,966 A * 7/1994 Bennett .............. A61N 1/36185 128/903

(Continued)

OTHER PUBLICATIONS

U.S. Appl. No. 62/370,113, by Bruce D. Gunderson, filed Aug. 2, 2016. 69 pgs.

(Continued)

*Primary Examiner* — Meredith Weare

(57) ABSTRACT

Systems, devices disclosed provide example methods comprising determining that a triggering event has occurred based on statuses for a set of physiological parameters associated with the patient, the physiological parameters indicative of the patient engaging in a patient initiated physical activity, generating a trigger output signal in response to the determination that the triggering event has occurred, wirelessly transmitting the trigger output signal to a pressure sensing device implanted in a vessel of the patient, triggering, based on receiving the trigger output signal, the pressure sensing device to sense a cardiovascular pressure of the patient; and transmitting, by the pressure sensing device, a wireless signal comprising data corresponding to the sensed cardiovascular pressure of the patient.

21 Claims, 20 Drawing Sheets

500
MONITOR INPUT PARAMETER(S) TO DETERMINE IF TRIGGERING EVENT HAS OCCURRED (502)
DETERMINE IF TRIGGER EVENT HAS OCCURRED (504) — NO / YES
DETERMINE IF MINIMUM TIME PERIOD HAS OCCURRED (506) — NO / YES
TRIGGER SENSOR CIRCUITRY TO TRANSITION TO SENSING MODE, SENSE PAP, AND TRANSMIT DATA (508)
TRANSITION SENSOR CIRCUITRY BACK TO LOW-POWER MODE (510)

(51) Int. Cl.

| | |
|---|---|
| ***A61N 1/39*** | (2006.01) |
| ***G16H 40/63*** | (2018.01) |
| ***G16H 20/30*** | (2018.01) |
| *A61B 5/024* | (2006.01) |
| *A61B 5/08* | (2006.01) |

(56) References Cited

U.S. PATENT DOCUMENTS

| | | | | |
|---|---|---|---|---|
| 5,545,186 | A | 8/1996 | Olson et al. | |
| 5,755,736 | A | 5/1998 | Gillberg et al. | |
| 6,438,408 | B1 | 8/2002 | Mulligan et al. | |
| 6,529,771 | B1 | 3/2003 | Kieval et al. | |
| 6,738,667 | B2 | 5/2004 | Deno et al. | |
| 6,764,446 | B2 * | 7/2004 | Wolinsky | A61B 5/0028 600/300 |
| 7,488,290 | B1 | 2/2009 | Stahmann et al. | |
| 8,864,676 | B2 | 10/2014 | Beasley et al. | |
| 2005/0027323 | A1 | 2/2005 | Mulligan et al. | |
| 2005/0065443 | A1 * | 3/2005 | Ternes | A61B 5/0006 600/509 |
| 2006/0041281 | A1 | 2/2006 | Von Arx et al. | |
| 2006/0224190 | A1 | 10/2006 | Gill et al. | |
| 2007/0088220 | A1 | 4/2007 | Stahmann | |
| 2007/0088221 | A1 | 4/2007 | Stahmann | |
| 2007/0156057 | A1 | 7/2007 | Cho et al. | |
| 2007/0161912 | A1 | 7/2007 | Zhang et al. | |
| 2008/0114407 | A1 | 5/2008 | Pastore et al. | |
| 2008/0171941 | A1 * | 7/2008 | Huelskamp | A61B 5/0031 600/484 |
| 2008/0177350 | A1 | 7/2008 | Kieval et al. | |
| 2008/0262361 | A1 | 10/2008 | Guffinger et al. | |
| 2009/0312650 | A1 | 12/2009 | Maile et al. | |
| 2010/0030292 | A1 | 2/2010 | Sarkar et al. | |
| 2010/0331713 | A1 * | 12/2010 | Ostrow | A61B 5/0031 600/518 |
| 2012/0283580 | A1 | 11/2012 | Havel et al. | |
| 2014/0276928 | A1 | 9/2014 | Vanderpool et al. | |
| 2016/0310031 | A1 | 10/2016 | Sarkar | |

OTHER PUBLICATIONS (PCT/US2017/068222 ) PCT International Search Report, dated Apr. 25, 2018, 4 pages.

* cited by examiner

EXERCISE TRIGGERED CARDIOVASCULAR PRESSURE MEASUREMENT

TECHNICAL FIELD

The disclosure relates to methods and systems to measure cardiovascular pressure.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads to position electrodes or sensors at a desired location or may be leadless, with the ability to wirelessly transmit data either to another device implanted in the patient or to another device located externally of the patient, or both.

Although implantation of some devices requires a surgical procedure (e.g., pacemakers, defibrillators, etc.) other devices may be small enough to be delivered and placed at an intended implant location in a relatively noninvasive manner, such as by a percutaneous delivery catheter. By way of illustrative example, implantable miniature sensors have been proposed and used in blood vessels to measure directly the diastolic, systolic and mean blood pressures, as well as body temperature and cardiac output. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such devices also, or alternatively, may be wirelessly linked to an external receiver. In addition, because these devices are implanted within a patient, battery life, the size of a battery or other on-board power sources for the device, and the ability or the difficulties associated with recharging the battery or other on-board power sources is an important consideration in determining what functions and features may be provided and/or may be available in any given system involving implanted medical devices.

SUMMARY

The disclosure describes implantable medical devices, systems, and associated techniques, structures, and assemblies configured to provide a triggered measurement of a patient's cardiovascular pressure. In some examples, triggering of these measurements may be done automatically, (e.g., without a trigger input initiated from an external source, for example based on a request initiated from the patient or by a physician from an external device), and based at least in part on monitoring one or more physiological parameters associated with the patient. Triggering the measurement of the blood pressure may occur when certain values, e.g., that exceed or fall within, i.e., satisfy the criteria defined by the threshold values/ranges for that particular parameter as related to these monitored of physiological parameters as these parameters values are detected and/or are derived from the monitored physiological parameters.

In some examples, one or more of the monitored physiological parameters are used as a basis to determine a status of input parameters. The status of input parameters is then used to determine when the patient being monitored is engaging in some form of exercise or other form of patient initiated physical activity. The determination that the patient is exercising or otherwise engaged in other patient initiated physical activity provides a time frame during which it may be desirable to measure a cardiovascular pressure of the patient, such as the patient's pulmonary artery pressure (PAP), and thus to generate a trigger output signal to have these blood pressure measurements taken. The triggering of the measurement of the patient's blood pressure may also be performed based on an input signal initiated by a user, such as the patient, a clinician, or a physician, the request provided as in input to an external device, such as a handheld programming device, which generates and transmits a signal to an implanted medical device implanted in the patient in order to trigger the implanted medical device to take cardiovascular pressure measurements of the patient.

The systems, devices, and method described herein provide techniques for automatically determining when a patient may be exercising or otherwise engaging in other types of patient initiated physical activities that would cause certain physiological characteristics to occur in a patient, such as an increased heart rate and an increase in respiratory rate, and then to automatically trigger sensing and recording of cardiovascular pressure of the patient based on that determination. The monitoring of physiological characteristics may be performed by a first implanted medical device implanted within the patient, and/or by sensors implanted and/or worn by the patient. When a determination has been made by the first implanted medical device that the patient is exercising or engaging in physical activates based on the monitored physiological characteristics, a trigger output signal may be generated by the first medical device. The trigger output signal is then wirelessly transmitted to a second sensor assembly that is configured to measure the cardiovascular pressure of interest when triggered, e.g., that is implanted in the patient's pulmonary artery and configured to measure PAP, and to transmit the data corresponding to the sensed blood pressures back to the first implanted medical device or an external computing device. Data transmitted back to the first implanted medical device may be further processed and stored for later retrieval by an external computing device.

Because of size restrictions, and thus limitations of the space available for a battery or other on-board power source needed to electrically power the implanted sensor assembly, particularly if placed within the patient's pulmonary artery, the sensor assembly may be configured to operate in a low-power mode until triggered, thus conserving the available on-board power of the sensor assembly, and to transition to a sensing mode when triggered by the trigger output signal. Once triggered, the sensor assembly transitions from the low-power mode to a sensing mode, and senses cardiovascular pressure to make one or more cardiovascular pressure measurements, e.g., within a predetermined window of time initiated by the trigger output signal. The sensor assembly is further configured to transmit data corresponding to the sensed pulmonary blood pressures to another device, e.g., back to the first implanted medical device. When sensing of the pulmonary blood pressures and transmission of the corresponding data is completed, the sensor assembly may return to the low-power mode until again triggered to take another set of cardiovascular pressure measurements.

Using the first implanted medical device to perform the monitoring of the physiological parameters and to make the determination of when to generate the trigger output signal allows this device to provide the electrical power required to perform these functions, and thus conserves the power of the sensor assembly implanted in the patient's pulmonary artery. The sensor assembly may be triggered into the mode that requirements more power drain, such as when sensing blood pressures and when transmitting data, only during the times deemed to be the most important times for taking the blood pressure measurements, while remaining in the low-power mode at other times, for example then the first medical device is providing the monitoring and determination functions. The ability for a user to also trigger the system provides a convenient technique for gather data related to a patient's blood pressure at times determined to be important by the user, while still allowing the sensor assembly to operate in the low-power mode as describe above at other times.

As an example, devices and system described herein may be configured to perform a method comprising determining, by processing circuity of an implantable medical device implanted in a patient, that a triggering event has occurred based on statuses for a set of physiological parameters associated with the patient, the physiological parameters indicative of the patient engaging in a patient initiated physical activity; generating, by a trigger circuitry of the implantable medical device, a trigger output signal in response to the determination that the triggering event has occurred; wirelessly transmitting, by a communication circuitry of the implantable medical device, the trigger output signal to a pressure sensing device implanted in a vessel of the patient; triggering, based on receiving the trigger output signal at a communication circuitry of the pressure sensing device, the pressure sensing device to sense a cardiovascular pressure of the patient; and transmitting, by the communication circuitry of the pressure sensing device, a wireless signal to the implantable medical device, the wireless signal comprising data corresponding to the sensed cardiovascular pressure of the patient.

Another example of devices and systems described herein is directed to an implantable medical device comprising processing circuitry configured to receive input signals from one or more sensors, the input signals comprising signals generated in response to measured physiological parameters associated with a patient, and to determine a status for each of a set of input parameters based on the measured physiological parameters, the status for each of the set of input parameters indicative of whether or not current value for the input parameter satisfies a threshold value for that input parameter; trigger circuitry configured to automatically generate a trigger output signal based at least in part on a determination that the statuses of the input parameters are indicative of the patient engaging in a patient initiated physical activity; communication circuitry configured to receive the trigger output signal generated by the trigger circuitry, and to wirelessly transmit the trigger output signal to a pressure sensing device that is implanted in a vessel of the cardiovascular system of the patient, the pressure sensing device configured to sense a cardiovascular pressure upon receipt of the trigger output signal.

Another example of devices and systems described herein is directed to an implantable pressure sensing device comprising; An implantable pressure sensing device comprising; a housing configured to be implanted in a vessel of a patient; a pressure sensor connected to the housing; pressure sensing circuitry within the housing; processing circuitry within the housing; and communication circuitry within the housing, wherein the communication circuitry is configured to receive a trigger output signal by wireless transmission, the trigger output signal generated by another implantable medical device in response to a monitored set of physiological parameters associated with the patient and having statuses indicative that the patient is engaging in a patient initiated physical activity, and wherein, in response to receipt of the trigger output signal, the processing circuitry is configured to trigger the sensing circuitry and pressure sensor to sense a cardiovascular pressure of the patient, and to transmit, by the communication circuitry, data corresponding to the sensed cardiovascular pressure of the patient.

Examples described in this disclosure are also directed to a system comprising a first implantable medical device implanted in a patient and comprising: processing circuitry configured to receive input signals from one or more sensors, the input signals comprising signals generated in response to monitoring a set of physiological parameters associated with a patient, and to determine a status for each of a set of input parameters based on current value determined for each of the set of physiological parameters, wherein at least one of the physiological parameters comprises an activity count, a heartrate, or a respiration rate; trigger circuitry configured to automatically generate a trigger output signal when the statuses of the input parameters are determined to indicate that a triggering event has occurred; and communication circuitry configured to receive the trigger output signal generated by the trigger circuitry, and to wirelessly transmit the trigger output signal; and a second implantable medical device comprising: a pressure sensing device that is implanted in the pulmonary artery of the patient and comprises a pressure sensor that is configured to sense a pulmonary artery pressure of the patient, and wherein upon receipt of the trigger output signal, the pressure sensing device is configured to transition from a low-power mode to a sensing mode, to sense pulmonary artery pressures of the patient over a predefined window of time, and to wirelessly transmit data corresponding to the sensed pulmonary artery pressure to the first implantable medical device while in the sensing mode, and upon completion of the sensing and transmission of the data, to transition back to the low-power mode.

Additional examples described in this disclosure are directed to a system comprising: a first implantable medical device implanted in a patient and comprising: processing circuitry configured to receive input signals from one or more sensors, the input signals comprising signals generated in response to monitoring a set of physiological parameters associated with the patient, and to determine a status for each of a set of input parameters based on current value determined for each of the set of physiological parameters, wherein the physiological parameters comprise an activity count, a heartrate, and a respiration rate; trigger circuitry configured to automatically generate a trigger output signal when the statuses of the activity count, the heartrate, and the respiration rate each exceeds a threshold level determined for each physiological parameter respectively, and logically ANDing the statuses of the activity count, the heart rate, and the respiration rate to generate the trigger output signal at times associated with the patient exercising or performing other physically exerting activities; and a communication circuitry configured to receive the trigger output signal generated by the trigger circuitry, and to wirelessly transmit the trigger output signal; and a second implantable medical device comprising: a pressure sensing device that is implanted in the pulmonary artery of the patient and comprises a pressure sensor that is configured to sense a pulmonary artery pressure of the patient, and wherein upon receipt of the trigger output signal, the pressure sensing device is configured to transition from a low-power mode to a sensing mode, to sense pulmonary artery pressures of the patient over a predefined window of time, and to wirelessly transmit data corresponding to the sensed pulmonary artery pressure to the first implantable medical device while in the sensing mode, and upon completion of the sensing and transmission of the data, to transition back to the low-power mode; wherein the communication circuitry of the first implantable medical device is configured to receive the wirelessly transmitted data corresponding to the sensed pulmonary artery pressure, and to transmit the data corresponding to the sensed pulmonary artery pressure to one or more external devices outside the patient.

It should be understood that although the invention is described principally in the context of triggering a sensor assembly implanted in a patient's pulmonary artery to sense pulmonary artery blood pressure, the invention is not limited to use in that context. The principles of the invention may be used to make implantable sensor assemblies configured to measure and monitor any of a variety of physiological parameters, and/or to adapt medical devices configured for delivery of therapy to perform one or more of these same functions.

BRIEF DESCRIPTION OF THE FIGURES

Throughout the specification, reference is made to the appended drawings, where like reference numerals designate like elements, and wherein.

DETAILED DESCRIPTION

Figure 1A:
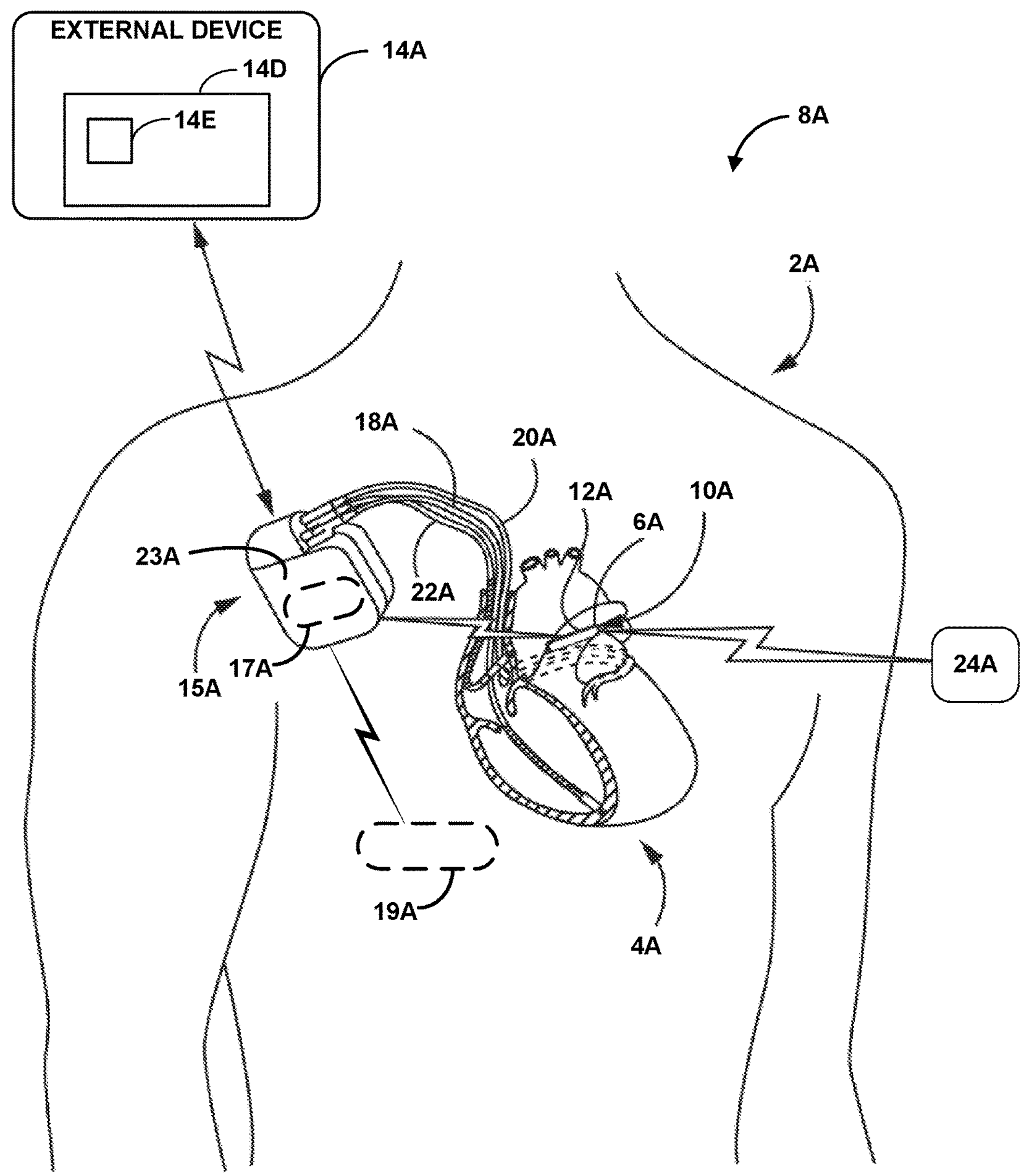
FIG. 1A is a conceptual drawing illustrating an example medical device system in conjunction with a patient according to various examples described in this disclosure.

Implantable miniature sensors have been proposed and used in blood vessels to measure directly the diastolic, systolic, and mean blood pressures, as well as body temperature and cardiac output. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, particularly patients suffering from chronic heart failure, may benefit from the use of implantable sensors configured to monitor blood pressures, including pulmonary blood pressures. Promising indications have been reported for using such implantable sensors.

A patient's blood pressure during periods of exercise or other physical activity may be quite different from the patient's blood pressure at times when the patient is inactive, such as when sleeping or sitting quietly. These differences in blood pressures, which may be measured during times of exercise or other physical activity by the patient, may be indicative of various health indicators and/or health issues that are not readily or easily detected or diagnosed by other techniques, such as blood pressure measurements taken related to the systemic blood pressure of the patient, or for example by monitoring various cardiovascular activates of the heart itself. In addition, the blood pressure measurements that exist during these times when the patient is exercising or is otherwise physically active may reveal information and can provide data that is not indicated or shown even by blood pressure data associated with blood pressures measured when a patient in not physically active. In various examples, the use of the phrase "blood pressure measurements" includes detection and/or sensing of a waveform sample associated with a patient's blood pressure over some predetermined period of time, for example over one second, or a longer period of time, for example twenty seconds.

Thus, the ability to accurately measure a patient's blood pressure, e.g., PAP, at times associated with a patient exercising or performing other more physically exerting activities can be valuable in accessing a patient's overall health condition, and in the monitoring and diagnosis of certain diseases or other health related conditions. For example, pulmonary hypertension may be a symptom of various circulatory, heart, and/or lung related conditions that are not easily diagnosed without the information related to the patient's pulmonary blood pressure, and in particular the patient's pulmonary blood pressure that exists under certain conditions, such as when a patient is exercising or is physically active. However, measuring a patient's PAP while the patient is ambulatory, for example while the patient is exercising or performing other more strenuous physical activities, is difficult or possible with conventional systems. For example, some conventional systems used to measure a patient's PAP require the patient to be lying down, or at least to be stationary while positioned next to an apparatus that is configure to communicate with the device sensing the PAP. Often, such measurements require placement of a sensing device in the patient's jugular vein, or some other vain, and thus is not conducive to allowing the patient to move about. As such, it may be difficult or impossible to get a PAP reading from the patient while the patient is exercising or otherwise physically active.

In addition, a device used to sense the patient's PAP may be a device that is implanted in the patient's pulmonary artery. However, because the sensor assembly that is implanted in the patient's pulmonary artery is necessarily restricted in physical size, and because it may be difficult to recharge the on-board power source included in the sensor assembly, and therefore conserving the available power on-board the sensor assembly is a significant concern in the operation of the implanted device. However, as described in this disclosure, a sensor assembly that is implanted in the patient's pulmonary artery and configured to sense the patient's PAP may operate in a low-power mode, conserving on-board power, and then when triggered, transition to a sensing mode, and take the PAP measurements. Once the PAP measurements have been taken, the sensor circuit may wirelessly transmit the data corresponding to the sensed pressures, and then return to the low-power operating mode until again triggered to take pressure measurements.

By using implanted devices as described herein, the systems, devices, and method of the present invention allow data related to a patient's blood pressure, e.g., PAP, to be automatically gathered and stored at times determined to be when the patient is engaging in the exercise or other physical activity at a predefined level of exertion. The level of exertion may be determined based on a set of physiological parameters and threshold values defined for that patient and monitored within the patient by a second implanted device. The automatic triggering of the collection of the data related to the pulmonary artery pressure can be accomplished by monitoring various physiological parameters associated with the patient, and triggering the collection of the pulmonary blood pressure measurements when it is determined that the patient is exercising or is otherwise physically active, and without the need for a user input to be made in order to trigger the process. This ability to automatically trigger the collection of this data provides a convenience to both the patient, and for example an assurance that the data is in fact more likely to actually be collected, because triggering is not reliant on any external input in order to provide the trigger that causes the measurement process to occur. The capability to set threshold values that are used to compare current values of the physiological characteristics of a patient, and then to determine a status for each of these physiological characteristics, allows a user, such as a physician, to set the level of exertion that will be needed to automatically trigger the sensing of the patient's pulmonary blood pressure when the predefined statuses for these physiological characteristics are present in the patient.

The present disclosure describes miniaturized and/or implanted devices that sense various physiological parameters of a patient, such as heartrate, respiration rate, and an activity count associated with the patient, and determine when to trigger taking pulmonary blood pressure measurements based on a status determined for each of the physiological parameters. The status of these physiological parameters may be set based on predefined thresholds that, when the threshold values for the physiological parameters are reached or satisfied, are deemed to indicate that the patient is exercising or is engaged in some minimum level of physical activity, and that taking pulmonary blood pressure measurement during these conditions is desirable. The data collected from the patient during these periods of exercise or other physical activity may be retrieved by the patient, by a clinician, and/or by a physician to determine and help monitor and/or diagnose various health issues associated with the patient, which in some circumstances would not be capable of being easily diagnosed or monitored without this data.

Such miniaturized and/or implanted devices may include a sensor assembly comprising a hermetic housing that contains a battery and electronics, and a fixation assembly, and may be implanted in a patient's pulmonary artery. The fixation assembly is provided to interface with the patient for stably positioning the device to achieve stable and durable sensing parameters. For proper function, the fixation assembly blends challenges of delivery through the vascular structure which includes tortuous pathways defined by the blood vessels of the patient. Therefore, there is a need for the fixation assembly to fit into a delivery system, such as a delivery catheter, for delivery, yet, the same fixation assembly needs to provide an appropriate fixation, once deployed in the body, and survive the long-term mechanical loading at the implant location. In some examples, such as a miniaturized device having a mechanical pressure sensor, additional challenges presented include the minimization of the forces that are transferred to a deformable membrane by the fixation.

FIG. 1A is a conceptual drawing illustrating an example medical device system 8A in conjunction with a patient 2A according to various examples described in this disclosure. Medical device system 8A is an example of a medical device system configured to implement the techniques described herein for monitoring physiological parameters of patient 2A, such as activity counts, heart rates, respiration rates, systemic blood pressures, body temperature(s), and body postures, and to determine whether to trigger sensing of pressure measurements of a cardiovascular pressure, e.g., PAP, of the patient. The determination regarding triggering in some examples is based at least in part on the current value(s) associated with one or more of these monitored physiological parameters. As illustrated, medical device system 8A comprises an implantable pressure sensing device, e.g., pressure sensing device 10A, and an implantable medical device (IMD) 15A. Pressure sensing device 10A is implanted, for example, in the patient's pulmonary artery 6A, through which blood flows from the patient's heart 4A to the lungs (not shown in FIG. 1A). For purposes of this description, knowledge of cardiovascular anatomy is presumed and details are omitted except to the extent necessary or desirable to explain the context of the present disclosure.

In various examples, pressure sensing device 10A comprises a sensor circuit 12A that is configured to sense pulmonary blood pressure, and to provide an electrical output signal indicative of the sensed blood pressure. In addition, pressure sensing device 10A is configured to be triggered, and when triggered, to sense one or more measurements of the blood pressure that are present within the patient's pulmonary artery. In various examples, pressure sensing device 10A is configured to operate in a low-power mode until triggered, and once triggered, to transition to a sensing mode during which sensor circuit 12A senses the blood pressure within the patient's pulmonary artery, for example over a predefined time period, e.g., a time window, and sensing the pulmonary blood pressure either continuously, or at some predetermined sample rate during the time window. Pressure sensing device 10A is further configured to transmit data corresponding to the sensed pulmonary blood pressures to one or more other devices, for example to IMD 15A.

In various examples, upon completion of both the sensing performed during the time window and transmission of the data associated with the sensed pressure measurements taken during the time window, pressure sensing device 10A may be configured to transition from the sensing mode back to the low-power mode, and to remain in the low-power mode until again triggered. In various examples, the trigger output signal used to trigger the pressure sensing device 10A is provided to pressure sensing device 10A by a wireless communication signal, the wireless communication signal transmitted by IMD 15A, or in some examples by another device external to pressure sensing device 10A, such as external device 14A. In various examples, pressure sensing device 10A comprises one or more timers (such as timer 212 shown in FIG. 7) that provide the timing associated with the time period that is included within the time window during which the blood pressure measurements are taken. In various examples, the length of time included in the time window is a parameter that is downloaded to and stored by pressure sensing device 10A via a wireless communication signal transmitted from an external device, such as external device 14A.

Figure 6:
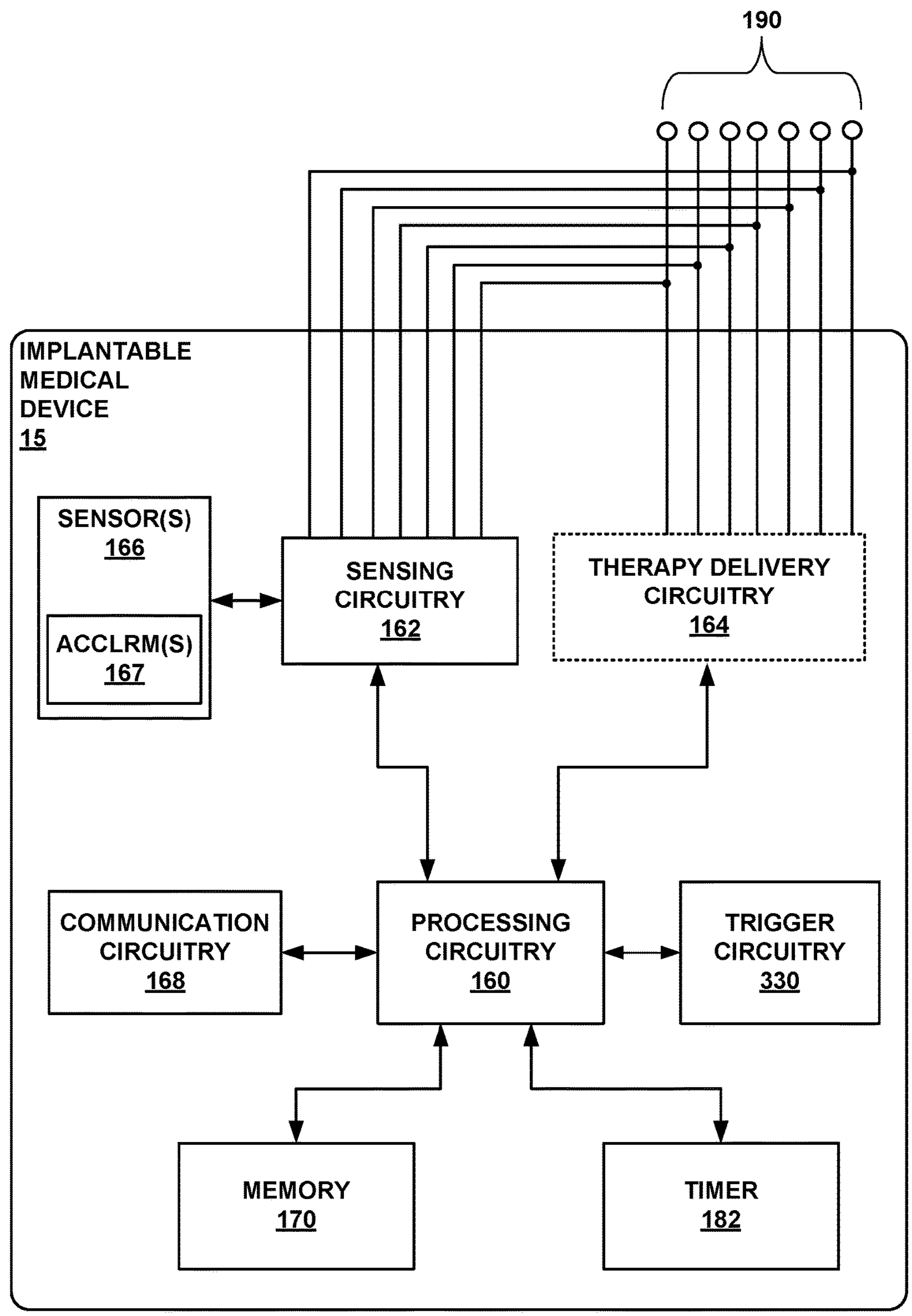
FIG. 6 is a functional block diagram illustrating an example configuration of an implantable medical device according to various examples described in this disclosure.

IMD 15A comprises another device of system 8A, and may be a pacemaker, cardioverter, defibrillator, or the like, that is also implanted within patient 2A, but at a location that is separate from the location of pressure sensing device 10A. In some examples, this disclosure may refer to IMD 15A as an "implantable monitoring device" or an "implantable hub device." IMD 15A may be coupled to one or more leads 18A, 20A, 22A carrying electrodes that are placed in electrical contact with selected portions of the cardiac anatomy of patient 2A in order to perform the functions of the IMD 15A, such as providing sensing functions and delivery of therapy, as is well known to those skilled in the art. For example, electrodes provided on leads 18A, 20A, and/or 22A may provide therapy, e.g., in the form of pacing stimulation or defibrillation shocks, to patient 2A. In various examples, one or more electrodes provided on leads 18A, 20A, and/or 22A may sense physiological parameters associated with patient 2A, e.g., such as cardiac electrical signals associated with the depolarization and repolarization of heart 4A or thoracic impedance, and generate electrical signals based on these sensed parameters, e.g., cardiac electrogram (EGM) signals, that are then processed by processing circuitry (not shown in FIG. 1A) of IMD 15A. Processing of the sensed electrical signals may be performed in order to measure and determine current values for one or more physiological parameters, such as heartrate and/or respiration rate associated with patient 2A. In various examples, a case 23A of IMD 15A is configured as an electrode that may form one or more circuit paths with the electrodes provided by leads 18A, 20A, and/or 22A for delivery of therapy, and/or for sensing physiological parameters associated with patient 2A. IMD 15A may include memory registers and/or one or more timers (for example memory 170 and timer 182 as shown in FIG. 6) that allow IMD 15A to perform various functions, including determining the calendar date and/or day, and the current time, along with providing timing functions as described throughout this disclosure.

Referring again to FIG. 1A, in various examples IMD 15A comprises one or more internal sensor circuits 17A configured to sense various parameters associated with patient 2A, including but not limited to sensing of physiological parameters associated with patient 2A, such as the heartrates, respiration rates, body temperatures of the patient 2A, and activity or motion, e.g., activity counts, based on various motions, such as steps taken by patient 2A. In various examples, sensor circuits 17A include one or more accelerometers that are configured to sense motions of patient 2A and/or the position (posture) relative to gravity of patient 2A. In various examples, sensor circuits 17A may receive signals provide by the electrodes located on one or more of leads 18A, 20A, and/or 22A, and process these received signals in order to generate sensed measurements and then to determine one or more current values of one or more physiological parameters associated with patient 2A. For example, a cardiac EGM signal may be provided to sensor circuits 17A via one or more of the electrodes located on leads 18A, 20A, and/or 22A, wherein the cardiac EGM signal is then processed by sensor circuits 17A and/or other circuitry provided in IMD 15A to generate current values for various physiological parameters, such as the patient's heartrate, respiration rate, and activity counts.

In various examples, one or more additional sensor circuits may be located outside of or separately located relative to the IMD 15A. These one or more additional sensor circuits are illustratively represented by sensor circuits 19A. Sensor circuits 19A may include a single sensor circuit configured to sense a particular physiological parameter associated with patient 2A, or may comprise a plurality of sensor circuits, which may be located at various and/or different positions relative to patient 2A and/or relative to each other, and are configured to sense one or more physiological parameters associated with patient 2A.

For example, sensor circuits 19A may include a sensor operable to sense a body temperature of patient 2A in a location of the sensor circuits 19A, or at the location of the patient where a temperature sensor coupled by a lead to sensor circuits 19A is located. In another example, sensor circuits 19A may include a sensor configured to sense motion, such as steps taken by patient 2A and/or a position or a change of posture of patient 2A. In various examples, sensor circuits 19A may include a sensor that is configured to detect breaths taken by patient 2A. In various examples, sensor circuits 19A may include a sensor configured to detect heartbeats, e.g., cardiac depolarizations, of patient 2A. In various examples, sensor circuits 19A may include a sensor that is configured to measure systemic blood pressure of patient 2A.

In some examples, one or more of the sensors comprising sensor circuits 19A may be implanted within patient 2A, that is, implanted below at least the skin level of the patient. In some examples, one or more of the sensors of sensor circuits 19A may be located externally to patient 2A, for example as part of a cuff or as a wearable device, such as a device imbedded in clothing that is worn by patient 2A. In various examples, sensor circuits 19A may be configured to sense one or more physiological parameters associated with patient 2A, and to transmit data corresponding to the sensed physiological parameter or parameters to IMD 15A, as represented by the lightning bolt coupling sensor circuits 19A to IMD 15A. Transmission of data from sensor circuits 19A to IMD 15A in various examples may be performed via wireless transmission, as would be understood by those of skill in the art. In various examples transmission of data from one or more of the sensors comprising sensor circuits 19A to IMD 15A may be performed by a wired connection between the sensor circuits 19A and IMD 15A.

IMD 15A may be configured to receive signals, wirelessly and/or through leads or other wired connections, from the sensor circuits 19A, the signals indicative of the sensed parameters being measured by the sensors of sensor circuits 19A. In various examples, IMD 15A is configured to receive signals from one or more of these sensors, and/or signals provided by the electrodes on leads 18A, 20A, and 22A, and/or signals provided by sensor circuits 17A, and to process the signals in order to determine, based at least in part on the received signals, if a trigger output signal should be generated to trigger the pressure sensing device 10A to begin taking pressure measurements of the blood pressure of the patient 2A, e.g., PAP measurement for patient 2A. In various examples, other parameters known or determined by processing circuitry of the IMD 15A, such as calendar date, time of day, and elapsed time since the last triggering of the pressure sensing device 10A to sense blood pressures may also be inputs to making the determination as to whether or not to trigger the pressure sensing device 10A to begin taking pressure measurements.

IMD 15A also may have wireless capability to receive and transmit, by telemetry, signals relating to operation of the device. For example, IMD 15A may be configured to wireless transmit a trigger output signal to pressure sensing device 10A, triggering sensor circuit 12A of pressure sensing device 10A to begin sensing pressures of the patient's pulmonary blood pressure of patient 2A, and to have the pressure sensing device 10A transmit back, for example by wireless communications to IMD 15A, data corresponding to the sensed pulmonary blood pressures. In various examples, IMD 15A stores the received data in memory (such as memory 170 mentioned above), for later retrieval and later transmission to an external device, such as external device 14A.

In various examples, IMD 15A may communicate wirelessly to an external device, such as external device 14A, or to other external devices, such as transceiver 24A. The pressure sensing device 10A may also be configured to communicate wirelessly with external device 14A or the transceiver 24A to provide in vivo data for selected physiological parameters to an external site, for example to output the data related to the pulmonary blood pressure measurements to these external device(s) directly. In various examples, external device 14A is a programming device, such as a handheld programmer, or for example a computer-type device such as hospital tablet 254 as illustrated and described with respect to FIG. 9. In various examples, external transceiver 24A as shown in FIG. 1A is an access point, such as access point 220 illustrated and described with respect to FIG. 8, that provides a wireless communication link between IMD 15A and/or pressure sensing device 10A and a network, such as network 222 also illustrated and described with respect to FIG. 8. As shown in FIG. 1A, external device 14A comprises a display 14D configured to display data, for examples data corresponding to pressure measurements taken by and transmitted from pressure sensing device 10A through IMD 15A or to external device 14A directly. Data corresponding to or derived from pulmonary blood pressure measurements taken by pressure sensing device 10A and displayed on display 14D is not limited to any particular data, or to any particular format for display of the data, and may comprise data displayed in graphic and/or tabular formats, for example as described and illustrated with respect to FIGS. 12A-12B.

In addition, system 8A may be configured to allow an external device, such as external device 14A, or transceiver 24A provided by an external network or computing device or system, to request (trigger), via an "Immediate" type request, the pressure sensing device 10A to take pulmonary blood pressure measurements and to transmit data corresponding to these pulmonary blood pressure measurements to IMD 15A and/or to external device 14A or to transceiver 24A. For example, button 14E of display 14D may include a touchscreen and an "Immediate" button that, when actuated by a user such as patient 2A or for example by a physician, provides a trigger output signal to pressure sensing device 10A, and triggers the pressure sensing device 10A to perform sensing of the patient's pulmonary blood pressure in response to receiving the request signal generated by actuation of the "Immediate" button.

Generation of a trigger output signal in response an "Immediate" request to measure pulmonary blood pressure is not limited to being generated by or provided from external device 14A, and for example may be generated by and/or transmitted from other external devices such as through transceiver 24A to IMD 15A and/or to pressure sensing device 10A. In some examples, the data corresponding to these pulmonary blood pressure measurements that were triggered by the "Immediate" request are transmitted by pressure sensing device 10A back to IMD 15A, to external device 14A, and/or to transceiver 24A. The request may also be programmed as a download to the external device 14A, which then allows the patient 2A to initiate the process.

For example, a physician may download the request wirelessly to the external device 14A, which then causes the external device 14A to display and/or provide an audio and/or a visual prompt to patient 2A via external device 14A with a message such as "your physician has requested that you perform an activity, please press the button when you are ready to begin." When patient 2A then press button 14E on external device 14A, the IMD 15A begins monitoring for compliance to the criteria that must be met by the statuses provided by the physiological parameters of the patient, for example for some predefined period of time, for example to allow the patient 2A to being exercising. If the criteria are met based on the statuses of the monitored physiological parameters within the predefined time period, sensing of the pulmonary blood pressure of patient 2A will be automatically triggered. In such cases, both the patient 2A and the physician making the request for the measurements may receive an indication transmitted from the IMD 15A or from pressure sensing device 10A that the requested pressure sensing session was successfully completed. If on the other hand, the criteria for triggering the taking of the pressure measurements are not met based on the status of the physiological parameters of patient 2A during the predefined time period, pressure sensing of the pulmonary blood pressure of patient 2A will not occur, and both the patient and the physician may receive an indication transmitted from the IMD 15A and/or the pressure sensing device 10A indicating that the requested pressure sensing session was not successfully completed.

The wireless communications described with respect to system 8A in FIG. 1A between any of the devices, such as IMD 15A, pressure sensing device 10A, external device 14A, and/or transceiver 24A are not limited to any particular wireless communication technique or protocol, and may include one or any combination of wireless communication techniques. Examples of communication techniques used by any of the devices described above with respect to FIG. 1A include radiofrequency (RF) telemetry, which may be an RF link established via Bluetooth, Bluetooth Low Energy, WiFi, or medical implant communication service (MICS). In some examples, IMD 15A and pressure sensing device 10A may communicate wirelessly via tissue conductance communication (TCC).

By virtue of being implanted within the pulmonary artery of patient 2A, pressure sensing device 10A is configured to provide accurate measurements of the pulmonary blood pressure for patient 2A, as compared for example to a sensor located outside the pulmonary artery of the patient. However, in order to be able to be implanted within the pulmonary artery itself, and also to minimize any significant undesirable effects on the blood flow through the pulmonary artery and to minimize or eliminate any patient discomfort that might be created by the implant, pressure sensing device 10A is generally constrained with respect to physical size and with respect to the shape of the device. These constraints also may limit size of a battery or other on-board power source that may be provided within pressure sensing device 10A for powering the circuitry of the device. Further, because of the particular location of pressure sensing device 10A as being implanted within the pulmonary artery, the depth, size restrictions, and orientation of the device may present additional restrictions and problems with respect to the ability to recharge a battery or some other on-board power source included within pressure sensing device 10A.

As such, battery life and the conservation of the available on-board power available from the battery or other on-board power source provided to electrically power the pressure sensing device 10A is a critical operating concern of system 8A. For example, a much higher level of power may be consumed by pressure sensing device 10A whenever sensor circuit 12A is sensing blood pressure measurements and/or when pressure sensing device 10A is transmitting data. The ability to trigger pressure sensing device 10A to take blood pressure measurements of the pulmonary blood pressure at particular times, for example when a patient is exercising, provides information related to pulmonary blood pressure at times and under patient conditions deemed to be important to taking measurements and to the diagnosis of the current condition of patient 2A. This feature allows the pressure sensing device 10A to remain idle, for example in a low-power mode, when the patient is in a state or condition, such as when sleeping, that would not be deemed to be as useful for taking pressure measurements as may be for example when the patient is exercising, but wherein pressure measurements taken during these times deemed to be less useful would still require a drain on the battery or other on-board power source provided within the pressure sensing device 10A.

On the other hand, IMD 15A may be implanted at location of the patient that allows the physical size of IMD 15A to be less constrained as compared to pressure sensing device 10A. As such, IMD 15A may also comprise a much larger battery or other on-board power source as compared to the battery or on-board power source of the pressure sensing device 10A. In addition, IMD 15A may be physically located and situated in a more easily discernable position and orientation after being implanted, for example just under the skin level of patient 2A, and thus is more easily amenable to various recharging techniques, such as inductive charging, that could be used to recharge and/or replenish the power level available from the battery or some other on-board power source provide to power IMD 15A.

Therefore, IMD 15A may be utilized to continuously power and/or receive signals from various sensors, such as signals provided by electrodes of lead 18A, 20A, and 22A, and sensor circuits 17A and 19A, and to process these received signals on a continuous basis or at regular intervals, without as much concern about battery/power source drain to the power source(s) provided in IMD 15A. Based on these processed signals, and in some examples additional information such as date and time information, IMD 15A may be configured to determine when to trigger pressure sensing device 10A to take pressure measures of the pulmonary blood pressure of patient 2A. In various examples, once the determination has been made to trigger pressure sensing device 10A, IMD 15A may also generate a trigger output signal that is wirelessly transmitted to pressure sensing device 10A, and upon receipt of the trigger output signal, triggers pressure sensing device 10A to perform the pressure measurements. Thus, IMD 15A, in conjunction with one or more signals provided by electrodes of lead 18A, 20A, and 22A, and/or sensor circuits 17A and/or 19A, may be used to monitor the physiological parameters associated with patient 2A, and to determine, based at least in part on current values of these physiological parameters, when to trigger pressure sensing device 10A. By only triggering pressure sensing device 10A to sense pulmonary blood pressures at selected times, such as when a determination has been made that the patient is exercising, system 8A may provide pulmonary blood pressure data when the patient is experiencing particular predefined physiological parameters, such as minimum current values for heartrate, respiration rate, activity counts, and or particular current values of other parameters such as posture, etc., and while conserving the power available on-board pressure sensing device 10A at other times.

In addition, because both pressure sensing device 10A and IMD 15A are implanted devices, they can move and operate according to the examples described herein on a continuous basis wherever patient 2A is located. As such, system 8A can be triggered to sense and provide data related to the patient's pulmonary blood pressure automatically, for example based on the monitored physiological parameters, without the need for any external triggering inputs and without the patient having to move to a location adjacent to externally located sensing apparatus. For example, a determination to trigger pressure sensing device 10A may be made based entirely on input parameters sensed directly from or derived from measurements made by electrodes and/or sensors included within or located on patient 2A, without the need for any inputs from outside these devices, for example inputs from the patient or from another person, such as a physician.

Further, the determination with respect to triggering pressure sensing device 10A can also be made, and pressure sensing device 10A may be triggered, when the patient is generally anywhere, and does not require the patient to be in a particular location or place, such as at a medical clinic or at a doctor's office. This provides system 8A with flexibility and convenience for the patient. For example, if a physician would like to have the blood pressure of patient 2A taken at a particular same time each day during the time the patient normally takes a walk, system 8A can be configured to trigger pressure sensing device 10A during that time period and automatically when the predefined conditions related to the physiological parameters of patient 2A have been met. The predefined conditions may be set up so that they are normally met at some point when the patient is taking this daily walk, based for example on threshold values being satisfied for heartrates, activity counts, and/or respiration rates being achieved. In this manner, the pulmonary blood pressure measurements will be taken automatically for that day once patient 2A is for example walking and the criteria for trigger pressure sensing device 10A have been met based at least in part on the sensed physiological parameters.

In addition, the ability of system 8A to provide measurements and data related to pulmonary blood pressure in the "immediate" mode, based on receiving an "immediate" request as described above, also provides a useful and convenient feature for both the patient and for others, such as a clinician or a physician caring for the patient. The ability of patient 2A to request blood pressure measuring in the "immediate" mode, and for example to see the data displayed on display 14D of external device 14A, allows the patient to make decisions based on the data. For example, based on the data, patient 2A may determine whether or not to take a particular medication, such as a diuretic medication, or a blood thinner or a blood pressure medication, and for example may allow the patient to adjust a dosage of a medication that is to be taken based on the blood pressure data provide by system 8A using the "immediate" mode. In addition, the "immediate" mode may also be useful and convenient for both the patient and another person, such as a clinician or a physician caring for the patient, by allowing pulmonary blood pressure measurements to be taken at a particular time and under particular conditions, such as when the patient is at a doctor's appointment and in the physical presence of the clinician or the physician. By using of the "immediate" mode, system 8A is configured to provide the most current data related to the patient's pulmonary blood pressure at a time and under specified conditions that can be controlled and dictated by the patient and/or the clinician or physician, thus providing a more flexible regime for monitoring, diagnosing, and treating various health related issues associated with patient 2A.

Figure 1B:
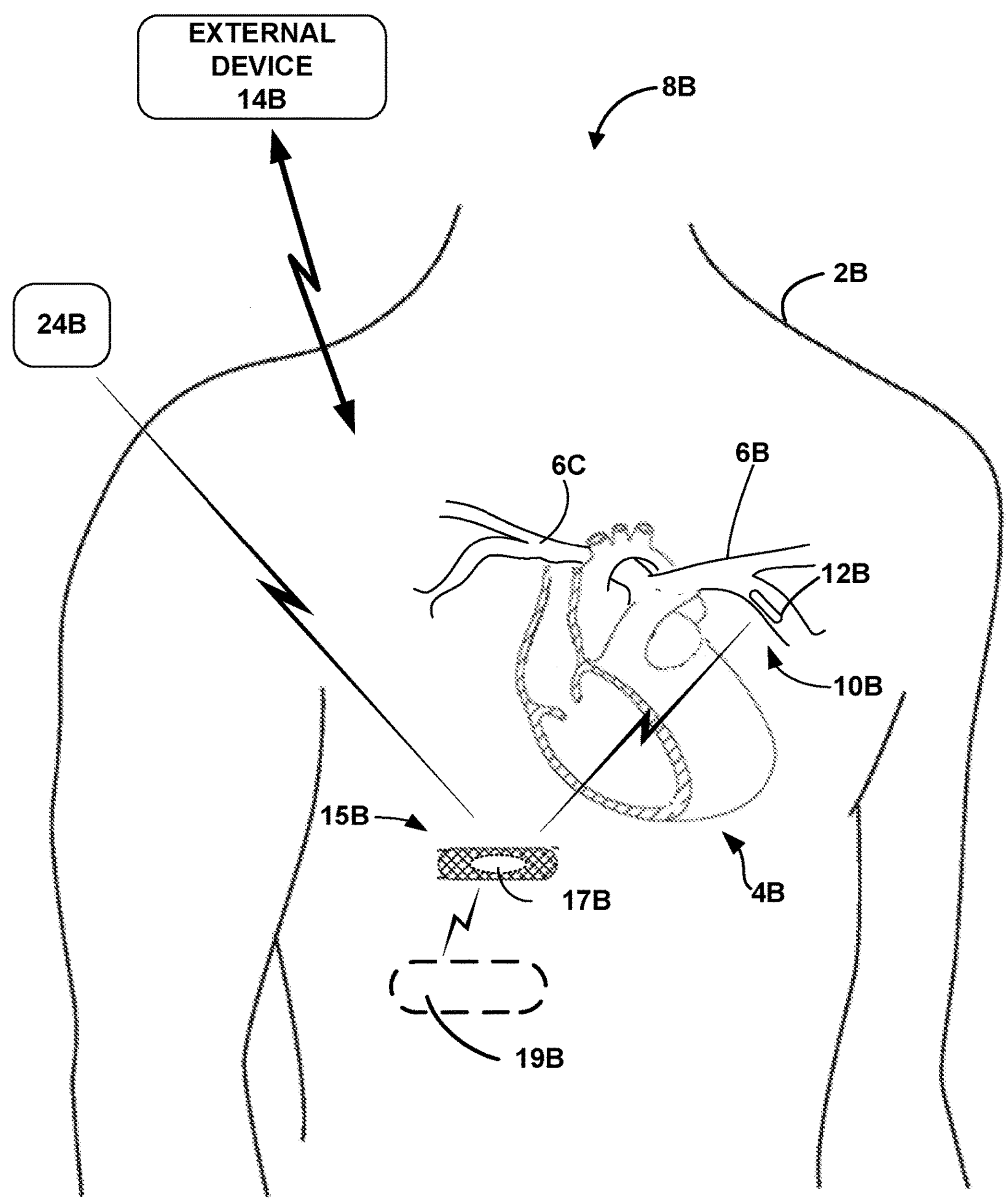
FIG. 1B is a conceptual drawing illustrating another example medical device system in conjunction with a patient according to various examples described in this disclosure.

FIG. 1B is a conceptual drawing illustrating another example medical device system 8B in conjunction with a patient 2B according to various examples described in this disclosure. Medical device system 8B is an example of a medical device system configured to implement the techniques described herein for monitoring physiological parameters of patient 2B, such as activity counts, heartrates, respiration rates, systemic blood pressures, and body movements and body postures, and determine whether to trigger sensing of the pulmonary blood pressure of patient 2B, the triggering based on, in some examples, the current value(s) associated with one or more of these monitored physiological parameters. As illustrated in FIG. 1B, medical device system 8B comprises an implantable pressure sensing device, e.g., pressure sensing device 10B, and an IMD 15B. Pressure sensing device 10B is implanted, for example, in the pulmonary artery 6B of patient 2A, through which blood flows from the heart 4B to the lungs (not shown in FIG. 1B). Again, for purposes of this disclosure, knowledge of cardiovascular anatomy is presumed, and details are omitted except to the extent necessary or desirable to explain the context of the present disclosure. In various examples, pressure sensing device 10B comprises sensor circuit 12B, and is configured to be triggered, and when triggered, to sense measurements of the blood pressure present in the pulmonary artery of patient 2B. In various examples, pressure sensing device 10B may be configured substantially similarly to pressure sensing device 10A, and may be configured to include and to provide any of the functions and features described with respect to pressure sensing device 10A, and any of the functions and features as otherwise described herein, and the equivalents thereof.

Medical device system 8B includes IMD 15B, which may comprise an insertable cardiac monitor (ICM) or an implantable hub device, in communication with external device 14B and/or transceiver 24B. In some examples, pulmonary artery 6B of heart 4B of patient 2B where pressure sensor assembly 10B is implanted may comprise a left pulmonary artery, in some examples more specifically the lower portion of the left pulmonary artery. In other examples, the pulmonary artery where pressure sensor assembly 10B is implanted may comprise a right pulmonary artery, illustrated as pulmonary artery 6C in FIG. 1B. For the sake of clarity, a fixation assembly for pressure sensing device 10B is not depicted in FIG. 1B. Examples of suitable fixation assemblies configured to secure pressure sensing device 10B within pulmonary artery 6B will be discussed below with respect to FIGS. 2A-4B.

In the illustrated example, IMD 15B comprises an ICM configured to sense, process, and record cardiac EGM signals from a position outside of heart 4B. IMD 15B may comprises one or more internal sensor circuits 17B configured to sense various parameters associated with patient 2B, including but not limited to sensing of physiological parameters associated with patient 2B, such as heartrates, respiration rates, body temperatures, and activity or motion, e.g., activity counts based on various motions, such as steps taken by patient 2B. Sensor circuits 17B may provide some or all of the features and functions described above with respect to sensor circuits 17A, and the equivalents thereof, but with respect to IMD 15B and system 8B. In various examples, one or more additional sensor circuits may be located outside of or separately located relative to the IMD 15B. These one or more additional sensor circuits are illustratively represented by sensor circuits 19B in FIG. 1B. Sensor circuits 19B may include a single sensor circuit configured to sense a particular physiological parameter associated with patient 2B, or may comprise a plurality of sensor circuits, which may be located at various and/or different positions relative to patient 2B and/or relative to each other, and are configured to sense one or more physiological parameters associated with patient 2B. Various examples of sensor circuits 19B are configured to provide some or all of the features and functions described above with respect to sensor circuits 19A and the equivalents thereof, but with respect to IMD 15B and system 8B as illustrated and described with respect to FIG. 1B. In addition, examples of system 8B may include a transceiver 24B communicatively coupled to IMD 15B, and may also be communicatively coupled to pressure sensing device 10B. Various examples of transceiver 24B are configured to perform some or all of the features and function described above with respect to transceiver 24A, and the equivalents thereof, but with respect to system 8B as illustrated and described with respect to FIG. 1B.

In system 8B, pressure sensing device 10B may be implanted within a pulmonary artery of patient 2B, and may include pressure sensing circuitry configured to measure the pulmonary artery pressure of patient 2B. IMD 15B may transmit data related to physiological parameter associated with patient 2B and as otherwise acquired or derived by IMD 15B to external device 14B and/or transceiver 24B. IMD 15B also may transmit cardiovascular pressure measurements received from pressure sensing device 10B to external device 14B and/or transceiver 24B. External device 14B, and/or transceiver 24B in conjunction with other external computer devices, may be used to program commands or operating parameters into IMD 15B for controlling the functions of IMD 15B, e.g., when configured as a programmer for IMD 15B. IMD 15B and may be configured to include and to provide any of the corresponding functions and features described with respect to IMD 15A with respect to monitoring physiologic signals, and with respect to determining when to trigger pressure sensing device 10B to sense pulmonary blood pressures of patient 2B in a manner similar to that described above with respect to IMD 15A and pressure sensing device 10A. IMD 15B in FIG. 1B may also provide any of the signal communications between pressure sensing device 10B, external device 14B, and transceiver 24B, as was described above with respect to IMD 15A, pressure sensing device 10A, external device 14A, and transceiver 24A, and the equivalents thereof.

Although FIGS. 1A and 1B illustrate example medical device systems 8A and 8B, respectively, that include a single pressure sensing device 10A, 10B, respectively, configured to communicate with an IMD 15A, 15B respectively, other examples may include two or more sensor assemblies configured to measure the same or different cardiovascular pressures of a patient when triggered by an implanted medical device such as IMD 15A or IMD 15B. Although primarily described herein in the context of PAP, other cardiovascular pressures may be measured in response to a trigger, such as other arterial, venous, or intracardiac pressures. Additionally, systems 8A, 8B may include additional or alternative implantable medical devices (IMDs), such as a pacemaker configured to be implanted entirely within heart of a patient, or an extravascular implantable cardioverter defibrillator configured to provide one or more of cardiac pacing, cardioversion, or defibrillation without an intravascular or intracardiac lead.

For the remainder of the disclosure, a general reference to a medical device system 8 may refer collectively to include any examples of medical device systems 8A and 8B, a general reference to a pressure sensing device 10 may refer collectively to include any examples of pressure sensing devices 10A and 10B, a general reference to sensor circuit 12 may refer collectively to include any examples of sensor circuits 12A and 12B, a general reference to an IMD 15 may refer collectively to include any examples of IMD 15A and 15B, a general reference to external device 14 may refer collectively to include any examples of external devices 14A and 14B, a general reference to sensor circuits 17 or sensor circuits 19 may refer collectively to include any examples of sensor circuits 17A, 17B, 19A, and 19B respectively, and a general reference to transceiver 24 may refer collectively to include any examples of transceivers 24A and 24B, and any equivalents thereof in all of these examples, as illustrated and described with respect to FIG. 1A and FIG. 1B.

FIGS. 2A-4B illustrate examples of a pressure sensing device 10 adapted for minimally invasive placement in a patient's blood vessel, the example pressure sensing device being shown in its expanded, deployment configuration. While the pressure sensing device as described with respect to FIGS. 2A-4B is referred to as "pressure sensing device 10," the examples illustrated in FIGS. 2A-4B may be illustrative of examples of the pressure sensing device 10A or 10B illustrated and described with respect to FIGS. 1A and 1B respectively, implantable pressure sensing device 10 as illustrated and described with respect to FIG. 7, implantable pressure sensing device 10 as illustrated and described with respect to FIG. 8, or implantable pressure sensing device 10 as illustrated and described with respect to FIG. 9, and may be configured to perform any of the functions and features as otherwise described herein, and the equivalents thereof as otherwise described with respect to these pressure sensing devices.

Figure 2A:
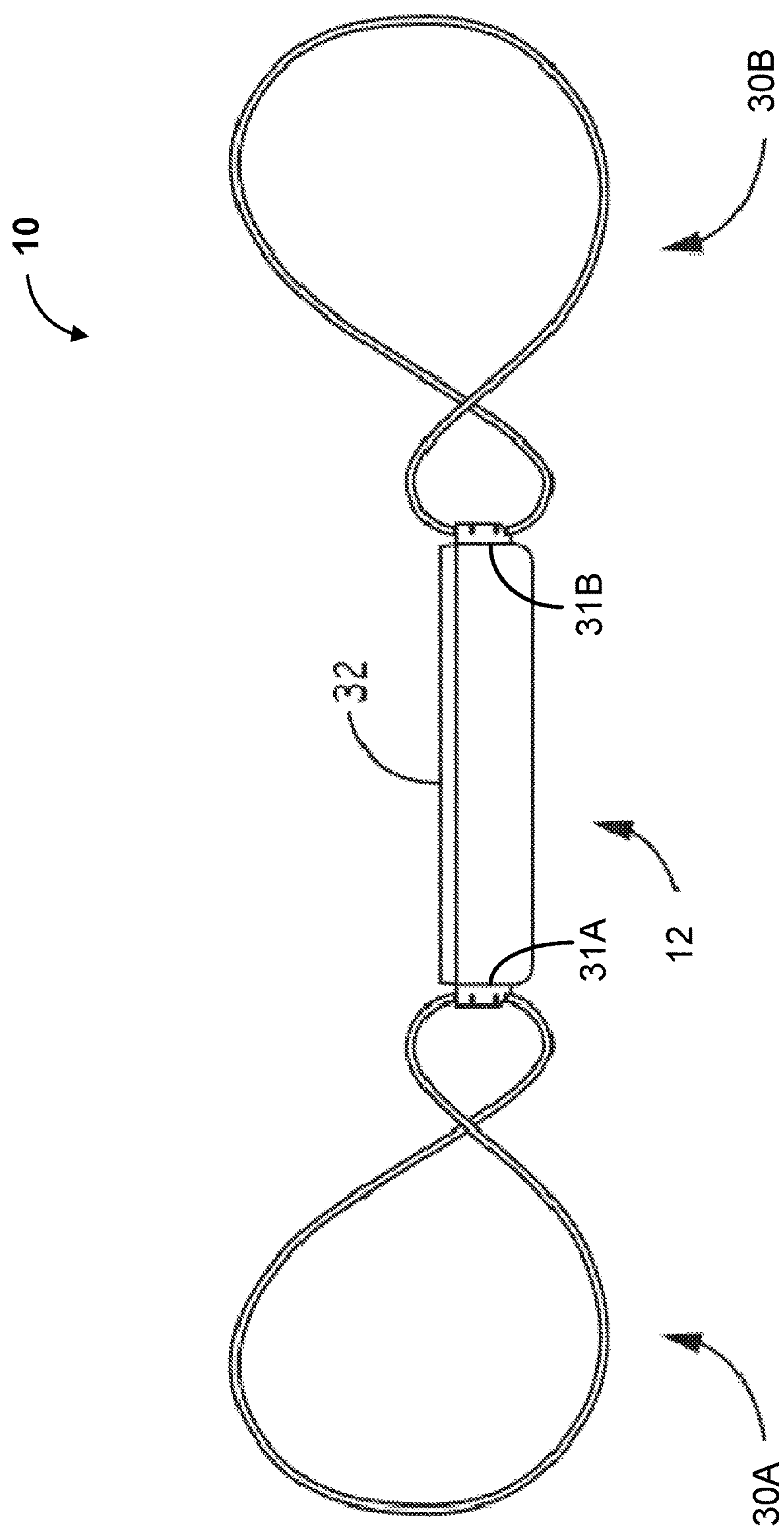
FIG. 2A a side profile view of a sensor assembly according to various examples described in this disclosure.

Turning first to FIG. 2A, a side profile view of a pressure sensing device 10 according to various examples described in this disclosure. The pressure sensing device 10 includes a sensor circuit 12 coupled to fixation members 30A, 30B (collectively "fixation assembly 30"). As illustrated in FIG. 2A, fixation member 30A is mechanically coupled to a first end 31A of pressure sensing device 10A, and fixation member 30B is mechanically coupled to a second end 31B of pressure sensing device 10. The fixation assembly 30 and sensor circuit 12 are arranged to enable the pressure sensing device 10 to be provided in a delivery configuration that enables it to be navigated to an implant location where it can be deployed into the deployment configuration. As described in this disclosure, it would be understood that the delivery configuration defines a pitch, width or diameter that is narrower, in relation to the deployment configuration, along a common plane. Upon release, the fixation assembly 30 expands into the deployment configuration so as to be in physical contact with the wall of the blood vessel into which the pressure sensing device 10 has been inserted in order to maintain the positional integrity of sensor circuit 12 within the blood vessel. In one example, the fixation assembly 30 will engage the interior wall of the vessel defining the blood flow lumen.

The sensor circuit 12 is attached to the fixation assembly 30 in a manner such that the sensor element 32 of the sensor circuit 12 is spaced from the wall of the vascular lumen to minimize adverse obstruction to blood flow through the lumen, and to position the sensor element 32 of the sensor circuit 12 to be fully exposed to the blood in the vessel, without obstruction from the housing of the sensor or the vessel wall. In various examples, sensor circuit 12 is configured to operate in a sleep mode, wherein the sleep mode provides a low-power consumption mode that conserves the battery power or other on-board power sources (not shown in FIG. 2A) included in sensor circuit 12. Sensor circuit 12 is further configured with a wireless transceiver (not shown in FIG. 2A), the wireless transceiver configured to receive a trigger output signal, and when the trigger output signal is received, to trigger sensor circuit 12 to sense, using sensor element 32, one or more blood pressure measurements associated with the blood pressure present in the blood vessel into which sensor circuit 12 has been located. In addition, the sensor circuit 12 is configured to receive an electrical signal generated by sensor element 32, and to determine one or more pressure values, in the form of sensed pressure data, based on the electrical signals generated by sensor element 32. Sensor circuit 12 is further configured to transmit the sensed pressure data, using the wireless transceiver, to one or more other devices (not shown in FIG. 2A), such as an IMD 15, and/or to other external devices, such as external device 14, and/or an external transceiver, such as transceiver 24.

In various examples, pressure sensing device 10 is configured to sense blood pressure measurements for a configurable predefined period of time, for example during a twenty-second time window, and to transmit the pressure sensor measurements taken during this predetermined period of time to other devices as described above, and then to return to the sleep or low-power mode until again receiving a trigger output signal from device external to pressure sensing device 10. Returning to the sleep or low-power mode enables pressure sensing device 10 to minimize the consumption of the available power, such as battery power or the on-board power source providing the power to operate pressure sensing device 10.

Figure 2B:
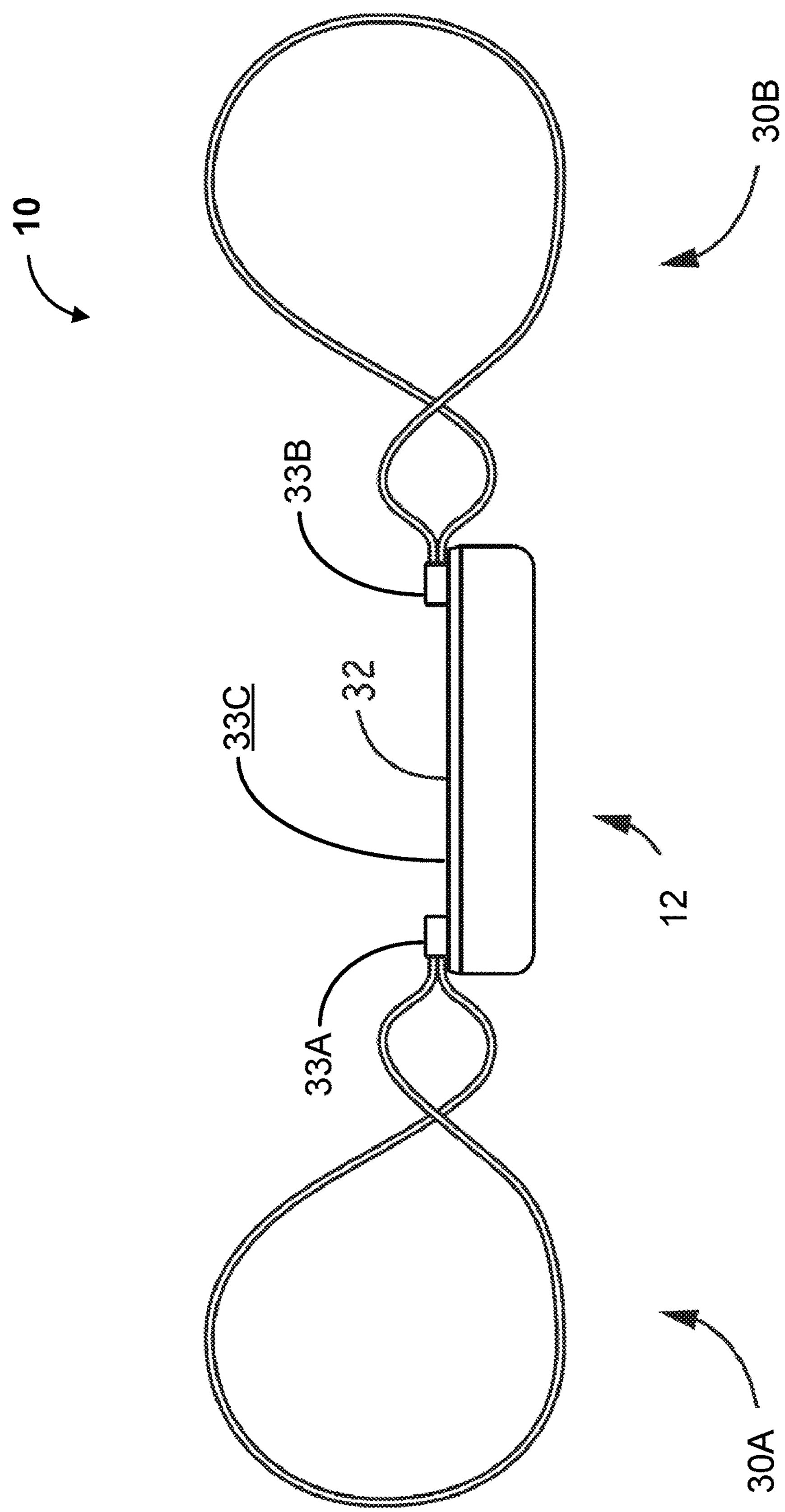
FIG. 2B is a side profile view of another example of sensor assembly according to various examples described in this disclosure.

FIG. 2B is a side profile view of another example of pressure sensing device 10 according to various examples described in this disclosure. The pressure sensing device 10 in FIG. 2B includes sensor circuit 12 coupled to fixation members 30A, 30B (collectively "fixation assembly 30"). As illustrated in FIG. 2B, fixation member 30A is mechanically coupled to a first end 33A of a top surface 33C of pressure sensing device 10, and fixation member 30B is mechanically coupled to a second end 33B of the top surface 33C of pressure sensing device 10. Examples of pressure sensing device 10 as illustrated in FIG. 2B may be configured to perform any or all of the features and functions described above with respect to sensor circuit 12 and FIG. 2A.

Figure 3A:
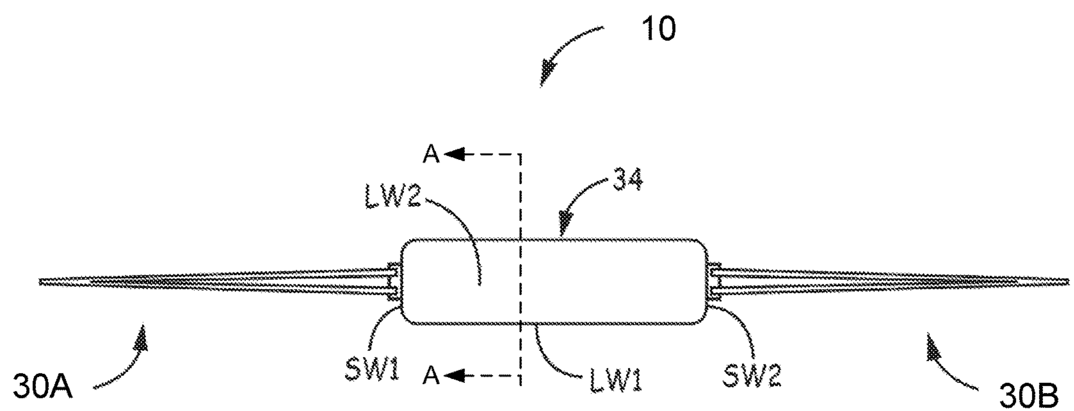
FIG. 3A illustrates a bottom perspective view of the sensor assembly of FIG. 2A according to various examples described in this disclosure.
Figure 3B:
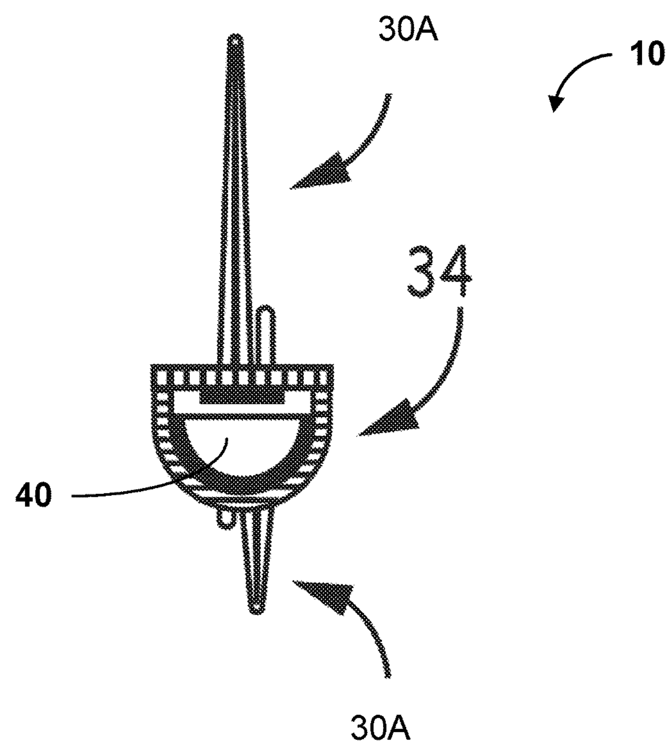
FIG. 3B illustrates a side cross-sectional view (A-A) of the sensor assembly of FIG. 2A according to various examples described in this disclosure.

FIG. 3A illustrates a bottom perspective view of the pressure sensing device 10, and FIG. 3B illustrates a side cross-sectional view (A-A) of the pressure sensing device 10. As illustrated in FIGS. 3A and 3B, pressure sensing device 10 includes a capsule 34 that forms a hermetically sealed housing that encloses the operational components, such as the sensor circuit 12, and a power source (not shown in FIG. 3A, but e.g., battery 40 shown in FIG. 3B) of the pressure sensing device 10. The capsule 34 defines longitudinal walls e.g., LW1, LW2, that extend from a first lateral side wall SW1 to a second lateral sidewall SW2. The longitudinal walls define the longitudinal axis of the pressure sensing device 10. As will be described in more detail with reference to FIGS. 4A and 4B, the fixation members 30A, 30B are coupled to an exterior of the capsule 34 such as the first and second sidewalls, respectively.

Figure 4A:
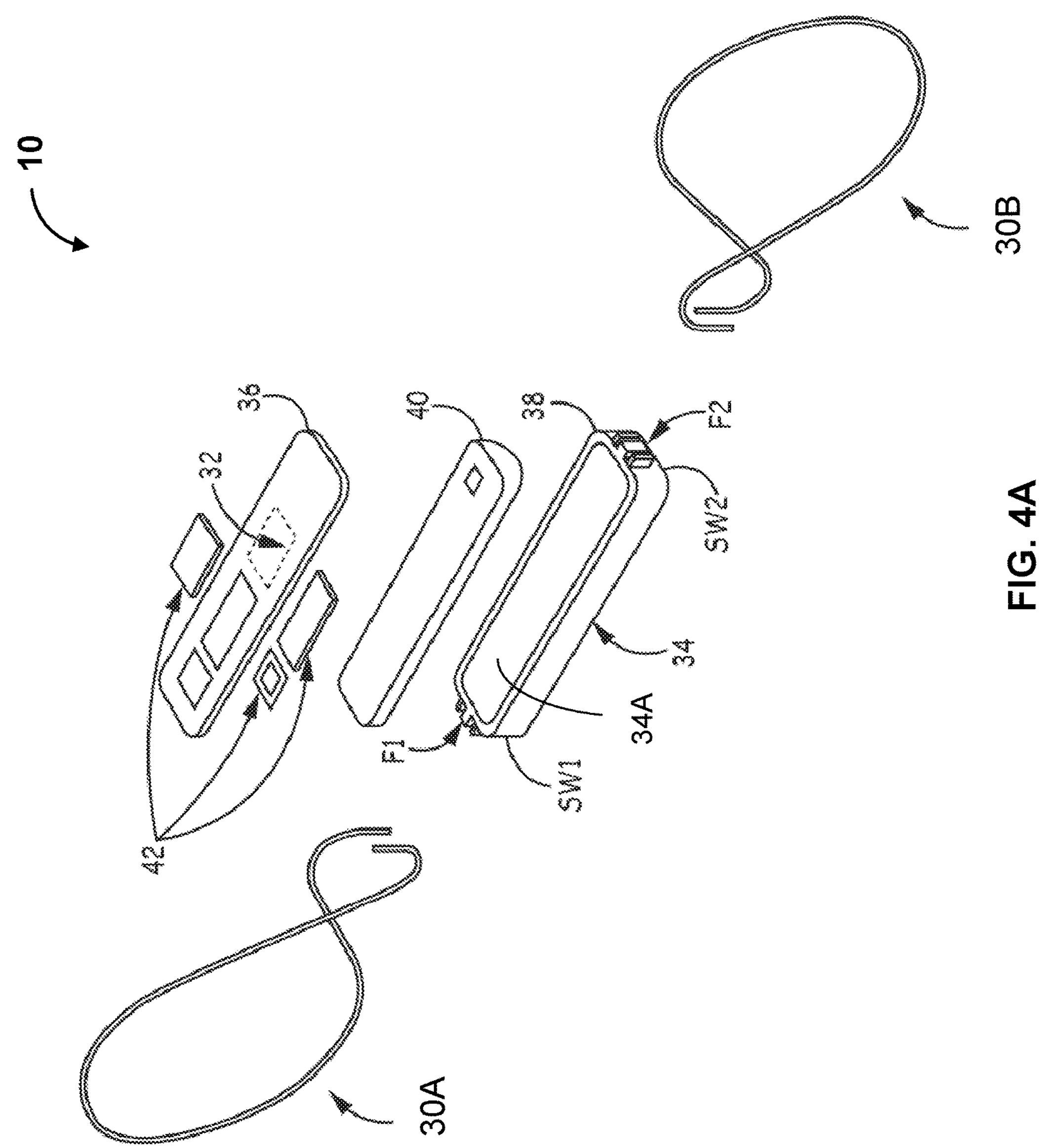
FIG. 4A is exploded perspective view of the sensor assembly of FIG. 2A according to various examples described in this disclosure.
Figure 4B:
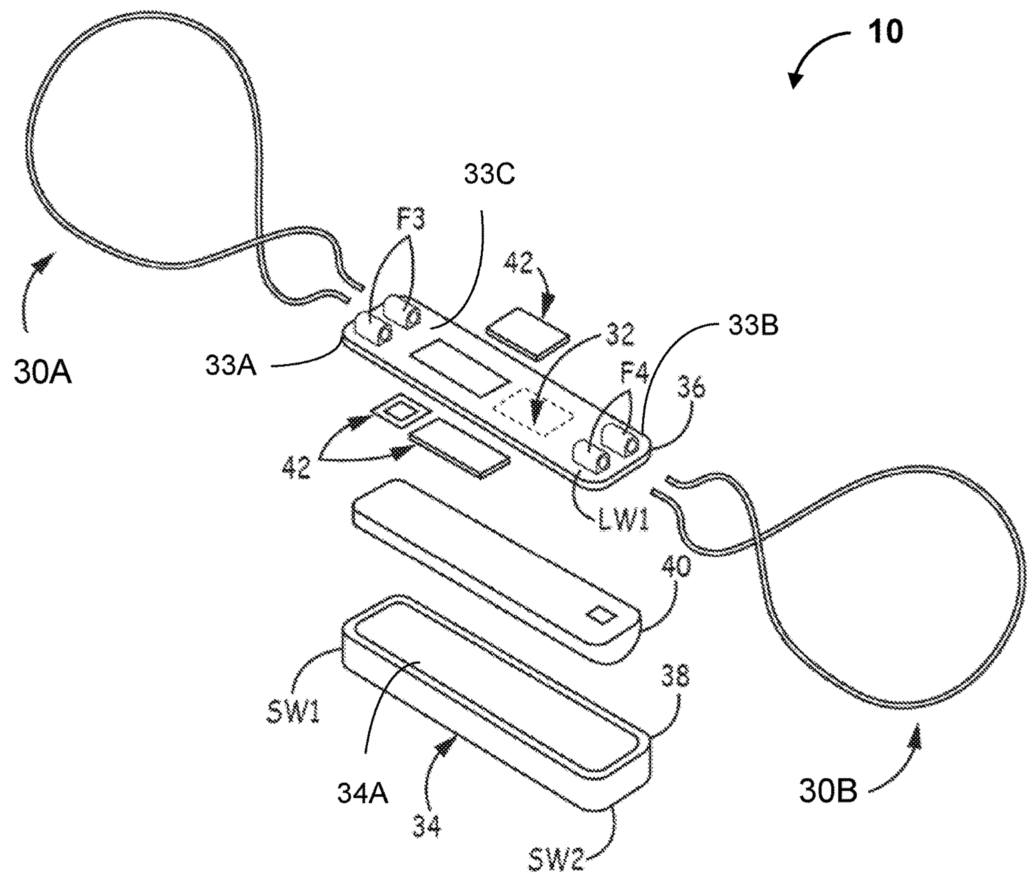
FIG. 4B is exploded perspective view of the sensor assembly of FIG. 2B according to various examples described in this disclosure.

FIGS. 4A and 4B are exploded perspective views of the pressure sensing device 10 in accordance with examples as described in this disclosure. As illustrated in FIGS. 4A and 4B, capsule 34 may include an elongate body that defines an interior cavity 34A. The interior cavity 34A of the capsule 34 is sized and shaped to contain the battery 40, and electronics and sensor components 42 of the sensor circuit 12. The capsule 34 is preferably designed with shapes that are easily accepted by the patient's body while minimizing patient discomfort. For example, the body of capsule 34 may be formed in a cylindrical shape with cylindrical sidewalls. Other non-cylindrical configurations may be employed, however, in which case the corners and edges may be designed with generous radii to present a capsule having smoothly contoured surfaces. In the depicted example, the body of capsule 34 is formed as a generally rectangular structure, which means that the outline of the shape of capsule 34 resembles a rectangle with the edges and corners that are contoured. In some examples, capsule 34 is formed having two sections 36, 38, one of which (e.g., section 36) can contain the sensor element 32, such as a pressure sensing diaphragm, of sensor circuit 12, while the other section (e.g., section 38) can contain the battery 40, and electronics and sensor components 42 of the sensor circuit 12.

In some examples, capsule 34 is formed from one or more biocompatible materials that can be hermetically sealed when the sections 36, 38 are joined. A number of such biocompatible materials may be employed, as will be understood by those familiar with the art, including metals and biocompatible plastics. For example, the sections 36, 38 may be formed from unalloyed titanium with an American Society for Testing and Materials (ASTM) grade 1 to grade 4 or an alloyed titanium (grade 5) that includes aluminum and vanadium. In some examples, section 36 may be formed of sapphire. For examples in which the sections are metal, the metal material of the capsule 34 may optionally be selected to be compatible with the fixation assembly 30 material so as to permit the fixation assembly 30 to be securely-coupled to the capsule 34. In other examples, the capsule 34 along with the fixation assembly 30 may be integrally formed from one or more of the same or distinct materials. In some examples, the capsule 34, as well as some portions of the fixation member 30, may be encapsulated in a biologically inert dielectric barrier material such as a film of silicone or polyp-xylylene) polymer sold under the trademark PARYLENE.

As shown in FIG. 4A, capsule 34 may include fasteners F1, F2, located on first side wall SW1 and second side wall SW2, respectively, that define channels for reception of a segment of the fixation assembly 30. In the example of FIG. 4B, capsule 34 may include fasteners F3, F4, located at a first end 33A and a second end 33B, respectively, of top surface 33C, wherein fasteners F3, F4 define channels for reception of a segment of the fixation assembly 30. The received segment may include a portion along a length of the fixation assembly 30, or a free end of the fixation assembly 30. The fasteners F1-F4 are coupled to an exterior of the capsule 34, or in alternative examples, formed integrally with the capsule 34. For example, as shown in the example of FIG. 4A, the fasteners F1, F2 are provided at an exterior of the capsule 34 at the lateral sidewalls SW1, SW2, respectively. In the alternative example of FIG. 4B, the fasteners F3, F4 are provided at spaced apart locations on an exterior of one or more of the longitudinal walls of the capsule 34, such as the bottom longitudinal wall LW2.

In some examples, the fasteners are formed as pairs of tabs that are arranged to define one or more channel(s) for receiving one or more segment(s) of the fixation assembly 30. Each fastener can include a pair of tabs that are aligned longitudinally as described, for example, in U.S. Pat. No. 8,864,676 to Beasley et al. which is incorporated herein by reference in its entirety. The fasteners may be coupled to the capsule 34 through welding, for example. Alternatively, the fasteners may be formed integrally with the capsule 34, preferably on opposing ends of the capsule. However, the description of the fasteners F1-F4 is not intended to be limiting, and rather, it is provided to explain the context of the disclosure. In some examples of FIGS. 4A-4B, the fasteners F1-F4 are formed as tubular structures that define channels that are sized to receive a segment of each of the fixation members 30A, 30B. In accordance with some examples, the fasteners F1-F4 may be formed as discrete components, such as tubes, for example, that can be coupled to the capsule 34 through coupling techniques such as welding or bonding agent such as glue or crimping. Alternatively, the fasteners may be formed integrally with the capsule 34. The fixation assembly 30 is coupled to the fasteners F1-F4 by any suitable coupling technique such as welding, crimping, bonding agent such as glue, frictional fit, etc.

The channels of fasteners F1-F4 may optionally be defined to receive a segment of the fixation members 30A, 30B in a snug fit arrangement to prevent relative movement between the capsule 34 and the fixation assembly 30. By way of dimensional example, the thickness of a cross section of fixation assembly 30 may be on the order of 0.006 inch for a round shape or 0.005 inch by 0.010 inch for a rectangular shape. In comparison, the diameter (or width) of the channel of each of the fasteners may be on the order of 0.010 inch to 0.025 inch. The free ends of each of the fixation members 30A, 30B may be oriented in opposing directions. For example, a first of the free ends may be oriented downward in relation to the lateral sidewall SW1, SW2, while the other end may be oriented upward in relation to the lateral sidewalls SW1, SW2 as shown in FIG. 4A. Among other things, such an orientation can provide a degree of load cancellation that minimizes load transfer to the sensor element 32. In alternative examples, one of the fixation members e.g., 30A may be coupled along a lateral sidewall such as SW1 as shown in FIG. 4A, and the other of the fixation members e.g., 30B may be coupled to a longitudinal wall such as LW1 or LW2 as shown in FIG. 4B.

Figure 5:
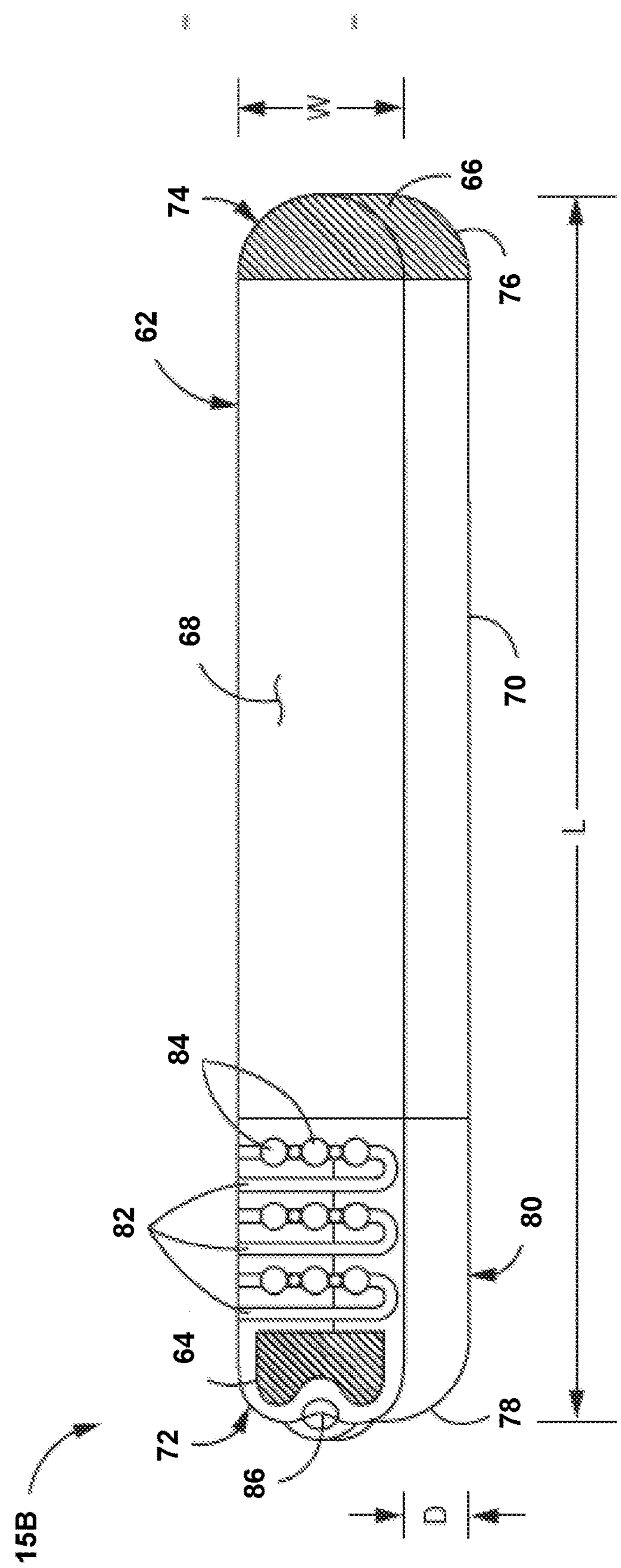
FIG. 5 is a conceptual drawing illustrating an example configuration of the implanted monitoring device of FIG. 1B according to various examples described in this disclosure.

FIG. 5 is a conceptual drawing illustrating an example configuration of ICM for IMD 15B of FIG. 1B. In the example shown in FIG. 5, IMD 15B may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the IMD 15B, and protects the circuitry contained therein from body fluids when IMD 15B is implanted in a patient. Electrical feedthroughs provide electrical connection of electrodes 64 and 66.

In the example shown in FIG. 5, IMD 15B may be defined by a length L, a width W and thickness or depth D and in some examples in the form of an elongated rectangular prism wherein the length L is much larger than the width W, which in turn is larger than the depth D. In one example, the geometry of the IMD 15B—in particular a width W greater than the depth D—is selected to allow IMD 15B to be inserted under the skin of the patient using a minimally invasive procedure and to remain in the desired orientation during insertion. For example, the device shown in FIG. 5 includes radial asymmetries (notably, the rectangular shape) along the longitudinal axis that maintains the device in the proper orientation following insertion. For example, in one example the spacing between proximal electrode 64 and distal electrode 66 may range from thirty millimeters (mm) to fifty-five mm, thirty-five mm to fifty-five mm, and from forty mm to fifty-five mm and may be any range or individual spacing from twenty-five mm to sixty mm. In addition, IMD 15B may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 68 may range from three mm to ten mm and may be any single or range of widths between three mm and ten mm. The thickness of depth D of IMD 15B may range from two mm to nine mm. In other examples, the depth D of IMD 15B may range from two mm to five mm and may be any single or range of depths from two mm to nine mm.

In addition, IMD 15B according to an example of the present disclosure is has a geometry and size designed for ease of implant and patient comfort. Examples of IMD 15B described in this disclosure may have a volume of three cubic centimeters (cm) or less, one-and-a-half cubic cm or less or any volume between three and one-and-a-half cubic centimeters. In addition, in the example shown in FIG. 5, proximal end 72 and distal end 74 are rounded to reduce discomfort and irritation to surrounding tissue once inserted under the skin of the patient. IMD 15B, including instrument and method for inserting IMD 15B may be configured as described, for example, in U.S. Patent Publication No. 2014/0276928, incorporated herein by reference in its entirety. In some examples, IMD 15B may be configured as described, for example, in U.S. Patent Publication No. 2016/0310031, incorporated herein by reference in its entirety.

In the example shown in FIG. 5, once inserted within the patient, the first major surface 68 faces outward, toward the skin of the patient while the second major surface 70 is located opposite the first major surface 68. Consequently, the first and second major surfaces may face in directions along a sagittal axis of patient 2A (see FIG. 1B), and this orientation may be consistently achieved upon implantation due to the dimensions of IMD 15B. Additionally, an accelerometer, or axis of an accelerometer, may be oriented along the sagittal axis.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the IMD 15B, and ECG data may be transmitted via integrated antenna 82 to another medical device, which may be another implantable device or an external device, such as external device 14B illustrated in FIG. 1B. Referring again to FIG. 5, in some examples, electrodes 64 and 66 may additionally or alternatively be used for sensing any bio-potential signal of interest, which may be, for example, an EGM, EEG, EMG, or a nerve signal, from any implanted location.

In the example shown in FIG. 5, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 5, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 5, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, IMD 15B may include electrodes on both major surface 68 and 70 at or near the proximal and distal ends of the device, such that a total of four electrodes are included on IMD 15B. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 5, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows IMD 15B to transmit and/or receive data. In other examples, integrated antenna 82 may be formed on the opposite major surface as proximal electrode 64, or may be incorporated within the housing 62 of IMD 15B. In the example shown in FIG. 5, anti-migration projections 84 are located adjacent to integrated antenna 82 and protrude away from first major surface 68 to prevent longitudinal movement of the device. In the example shown in FIG. 5 anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 5 header assembly 80 includes suture hole 86, which provides another means of securing IMD 15B to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of IMD 15B.

FIG. 6 is a functional block diagram illustrating an example configuration of an IMD 15 according to various examples described in this disclosure. IMD 15 may correspond to any of IMD 15A in FIG. 1A, IMD 15B in FIG. 1B and FIG. 5, or another IMD configured to implement the techniques as described herein. In the illustrated example, IMD 15 includes processing circuitry 160 and an associated memory 170, sensing circuitry 162, therapy delivery circuitry 164, one or more sensors 166, and communication circuitry 168. However, IMD 15 need not include all of these components, or may include additional components. For example, IMD 15B may not include therapy delivery circuitry 164 in some examples.

Memory 170 includes computer-readable instructions that, when executed by processing circuitry 160, cause IMD 15 and processing circuitry 160 to perform various functions attributed to IMD 15 and processing circuitry 160 herein (e.g., determining time of day, comparing time of day to a predetermined window, determining posture, comparing posture to target posture, and causing communication circuitry 168 to transmit cardiovascular pressure measurements to an external device, storing current values and threshold values for physiological parameters and status associated with enable/disable flags and/or timer statuses, and generate a trigger output signal). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 170 may store threshold(s) for time of day, posture, heart rate, activity level, respiration rate, and other parameters. Memory 170 may also store data indicating cardiovascular pressure measurements and cardiovascular pressure waveforms.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 6 may correspond to, for example, electrodes located on leads 18A, 20A, 22A of IMD 15A (FIG. 1A), or proximal electrode 64 and distal electrode 66 of IMD 15B (FIGS. 1B and 5). Sensing circuitry 162 may monitor signals from a selected two or more of electrodes 190 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190. In some examples, sensing circuitry 162 may sense or detect physiological parameters, such as heart rate, blood pressure, respiration, and other physiological parameters associated with a patient.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

In the example of FIG. 6, IMD 15 includes one or more sensors 166 coupled to sensing circuitry 162. Although illustrated in FIG. 6 as included within IMD 15, one or more of sensors 166 may be external to IMD 15, e.g., coupled to IMD 15 via one or more leads, or configured to wirelessly communicate with IMD 15. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers 167, e.g., one or more three-axis accelerometers. Signals generated by the one or more accelerometers 167 may be indicative of, as examples, gross body movement (e.g., activity) of the patient, patient posture, heart sounds or other vibrations or movement associated with the beating of the heart, or coughing, rales, or other respiration abnormalities. Accelerometers 167 may produce and transmit signals to processing circuitry 160 for a determination as to whether the patient is in a target posture. In various examples, signals from the accelerometers 167 are processed to determine an activity, such as when the patient is taking a step or steps, or for example when the patient is running, used to provide an activity count associated with patient initiated physical activity of the patient. In various examples, the target posture determined for a patient may be used as a verification of an activity that is associated with an activity count for the patient. For example, activities that might be construed as a patient walking or running may only be verified for used in determining a current value for an activity count if the patient is also determined to be in a standing or otherwise upright posture. Such a verification based on posture may be used to discard or disregard accelerometer reading that for example resulting from a patient riding in a car on a bumpy road that might otherwise be interpreted as walking or taking steps. In some examples, sensors 166 include one or more microphones configured to detect heart sounds or respiration abnormalities, and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals. In various examples, sensors 166 may include one or a combination of sensors 17 and 19 as previously described.

In some examples, processing circuitry 160 determines one or more patient parameter values based on pressure signals. Patient parameter values determined based on pressure may include, as examples, systolic or diastolic pressure values, such as pulmonary artery diastolic pressure values. In some examples, a separate device such as sensor circuits 17 or 19 include one or more sensors and sensing circuitry configured to generate a pressure signal, and processing circuitry 160 determines patient parameter values related to blood pressure based on information received from IMD 15.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

Memory 170 may store information relating to the predetermined window of time for cardiovascular pressure measurements. Memory 170 may also store data related to cardiovascular pressure measurements, such as the pressure values and the corresponding times of day of the patient activities. Memory 170 may also store information relating to the threshold values for one or more physiological parameters used to determine when a trigger output signal should be generated to trigger cardiovascular pressure measurements, such as thresholds for signals from accelerometers 167 and threshold values related to measured and/or derived values based on signals provided by sensors 166.

Processing circuitry 160 may determine the time of day using timer 182. Timer 182 may be keep a running count based on a voltage-controller oscillator or any other suitable oscillator or clock. Timer 182 may generate an alert to processing circuitry 160 when the time of day is within the predetermined window of time for cardiovascular pressure measurements.

Communication circuitry 168 includes any suitable hardware, firmware, software or any combination thereof for communicating with another device, such as an external device 14, transceiver 24, or another IMD or sensors, such as sensor circuits 19, as shown in FIG. 1A and FIG. 1B respectively. Under the control of processing circuitry 160, communication circuitry 168 may receive downlink telemetry from and send uplink telemetry to external device 14 or another device with the aid of an antenna, which may be internal and/or external. In some examples, communication circuitry 168 may communicate with a local external device, for example through transceiver 24, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 15 using external device 14 or another local or networked computing device configured to communicate with processing circuitry 160 via communication circuitry 168, for example through a transceiver such as transceiver 24. The clinician may also program parameters of IMD 15 using external device 14 or another local or networked computing devices. In some examples, the clinician may select patient parameters used to determine times of day and target activity levels to determine when to trigger taking cardiovascular pressure measurements.

In various examples, processing circuitry 160 is configured to receive signals from sensing circuitry 162, sensors 166, and or sensor signal provided by sensors external to IMD 15, to process these sensor signals to generate one or more input parameters based either directly on or derived from the sensor signals. The input parameters are associated with current value(s) for one or more physiological parameters associated with a patient, such as patient 2A or 2B. The physiological parameters associated with the input parameters may include activity counts, respiration rates, breathing rates, movements, postures, and changes in postures associated with a patient. The current values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period. Similarly, current values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time.

In various examples, these current values may be stored in memory 170, and updated on some time-to-time basis, based in some examples on the sampling rate and/or some other characteristic (e.g., rate of change) of the characteristics associated with that particular input parameter. For example, current value of the patient's body temperature may not change as quickly as the current value for the patient's heart rate, and thus may not need to be updated as often at the current value for the heartrate. In addition to current values, memory 170 may also be configured to store one or more predetermined threshold values associated with the input parameters. In various examples, IMD 15 comprises a trigger circuitry 330 coupled to processing circuitry 160. Trigger circuitry 330 may be configured to receive the current values and/or some other form of status values based on the current values that are stored in memory 170, and at least in part based on these current values and/or status values, determine whether or not to generate a trigger output signal. For example, a status value for a particular input parameter may be determined based on whether the current value for the input parameter satisfies the criteria set by the threshold value, for example when the current value exceeds, is less than, and/or is out of range of values provide as the threshold value(s) for that input parameter. In some examples, trigger circuitry 330 also bases the decision of whether or not to generate the trigger output signal on additional information or instead of the current values and or the status values. For example, trigger circuitry 330 may require a minimum time period to have expired, as provided by an output from timer 182, before generating another trigger output signal, regardless of the status of the input parameters. In various examples, and indication that an "immediate" request signal (as described above) has been received by IMD 15, may be used, without or without consideration of the status of other inputs being provided to trigger circuitry 330, to make the determination that a trigger output signal should be generated. Further examples and illustrations with respect to the operation of trigger circuitry 330 are illustrated and described with respect to FIGS. 10A-B and FIG. 11.

If trigger circuitry 330 determines that a trigger output signal is to be generated, trigger circuitry 330 may be configured to generate the trigger output signal, and to provide the trigger output signal to processing circuitry 160 for further processing, and then to be transmitted wirelessly, for example by communication circuitry 168, to a pressure sensing device, such as pressure sensing device 10, that is located externally to IMD 15 and the can carry out the requested pressure sensing operations. Once the pressure sensing device has completed the pressure sensing operations, IMD 15 is configured to receive the data corresponding to these pressure measurements via communication circuitry 168 as the data is transmitted by the pressure sensing device back to IMD 15. In various examples, the received data may or may not be further processed by processing circuitry 160, and then stored in memory 170 for later retrieval. Communication circuitry 168 may later retrieve this data from memory 170, and wirelessly transmit the data to one or more devices that are external to IMD 15 and that are also external to the patient. In the alternative, if the trigger circuitry 330 determines that a trigger output signal is not to be generated at the present time, trigger circuitry 330 may continue to monitor the current values, and the statuses associated with the current values, and/or addition information, such as the status stored in any enable/disable registers in memory 170 and/or the status of an output provided by timer 182, to determine when a trigger output signal should be generated at some point in time.

Figure 7:
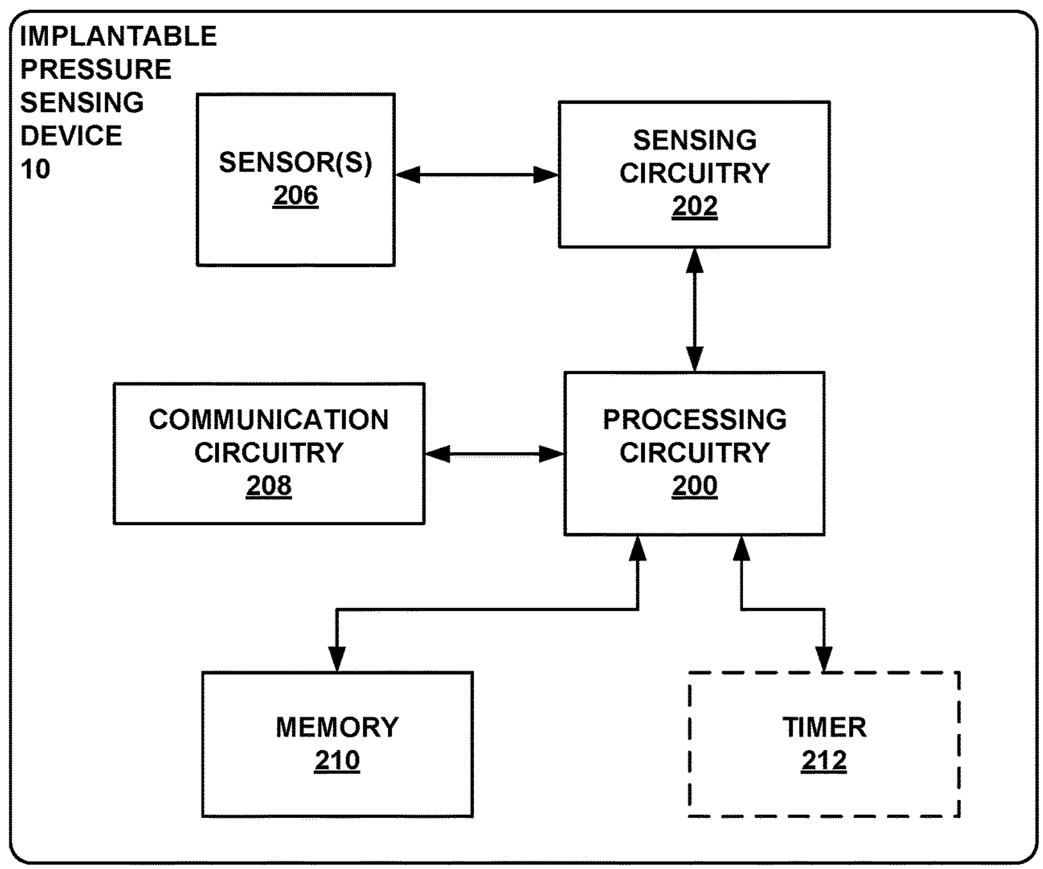
FIG. 7 is a functional block diagram illustrating an example configuration of implantable pressure sensing device according to various examples described in this disclosure.

FIG. 7 is a functional block diagram illustrating an example configuration of implantable pressure sensing device 10 (hereinafter "pressure sensing device 10"). Pressure sensing device 10 may comprise any examples of pressure sensing device 10A and sensor circuit 12A in FIG. 1A, pressure sensing device 10B and sensor circuit 12B in FIG. 1B, pressure sensing devices 10 in FIGS. 2A-4B, or another pressure sensing device configured to implement the techniques for measuring blood pressures as described in this disclosure, and the equivalents thereof. In the illustrated example, pressure sensing device 10 includes processing circuitry 200 and an associated memory 210, sensing circuitry 202, one or more sensors 206, communication circuitry 208, and an optional timer 212. However, pressure sensing device 10 need not include all of these components, or may include additional components.

Memory 210 includes computer-readable instructions that, when executed by processing circuitry 200, causes pressure sensing device 10 and processing circuitry 200 to perform various functions attributed to pressure sensing device 10 and processing circuitry 200 herein (e.g., determining time of day, comparing time of day to a predetermined window, causing communication circuitry 208 to receive triggering signals from another device, causing communication circuitry 208 to transmit cardiovascular pressure measurements to the other device). Memory 210 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 210 may store threshold(s) for time of day and other parameters. Memory 210 may also store data indicating cardiovascular pressure measurements and cardiovascular pressure waveforms.

Processing circuitry 200 may include fixed function circuitry and/or programmable processing circuitry. Processing circuitry 200 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 200 may include multiple components, such as any combination of one or more microprocessors, one or more controllers, one or more DSPs, one or more ASICs, or one or more FPGAs, as well as other discrete or integrated logic circuitry. The functions attributed to processing circuitry 200 herein may be embodied as software, firmware, hardware or any combination thereof.

Sensors 206 may include pressure sensors, e.g., capacitive, piezoresistive, piezoelectric, electromagnetic, or optical pressure sensors, configured to sense blood pressures and to transduce the sensed blood pressure into electrical output signals. In some examples, sensors 206 may sense or detect physiological parameters such as pulmonary blood pressure in the pulmonary system of a patient in examples where the pressure sensing device 10 may be implanted in a pulmonary artery of the patient. Sensing circuitry 202 may receive the electrical output signal signals from sensors 206, and further process the electrical output signals, for example by performing any of filtering, amplification, signal conditioning, and/or analog to digital conversion of the electrical output signal to provide one or more processed signals. In some examples, processing circuitry 200 is configured to receive the processed signals, and to determine one or more patient parameter values based on the processed signals. Patient parameter values determined based on pressure may include, as examples, systolic or diastolic pressure values, such as pulmonary artery diastolic pressure values. Processing circuitry 200 may also store the raw or processed pressure signals in memory 210.

Communication circuitry 208 includes any suitable hardware, firmware, software or any combination thereof for communicating with another device, such as IMD 15 or another IMD or sensor. Under the control of processing circuitry 200, communication circuitry 208 may receive downlink telemetry from and send uplink telemetry to external device 14, or another device such as transceiver 24, with the aid of an antenna, which may be internal and/or external. In some examples, communication circuitry 208 may communicate with a local external device, and processing circuitry 200 may communicate with a networked computing device via the local external device and a computer network, such as the Medtronic CareLink® Network developed by Medtronic, plc, of Dublin, Ireland. Communication circuitry 208 may be configured to receive a triggering signal from another device. In response to the triggering signal, processing circuitry 200 may control sensor(s) 206 and sensing circuitry 202 to measure cardiovascular pressure. Communication circuitry 208 may be further configured to transmit data corresponding to and/or derived from the cardiovascular pressure measurements, including a pressure waveform.

Processing circuitry 200 may determine the time of day using and optional timer 212. Optional timer 212 may be keep a running count based on a voltage-controller oscillator or any other suitable oscillator or clock. Optional timer 212 may generate an alert to processing circuitry 200 when the time of day is within the predetermined window of time for cardiovascular pressure measurements.

Pressure sensing device 10 may be configured to operate in a low-power or sleep mode until receiving a trigger output signal, as described above, and then to switch to a sensing mode. While in the sensing mode, pressure sensing device 10 may perform any of the pressure sensing, data processing, and data transmission functions as described herein. Once these sensing and data transmissions operations are completed, pressure sensing device 10 may return to the low-power or sleep mode in order to conserve power until pressure sensing device 10 again receives a trigger output signal.

Figure 8:
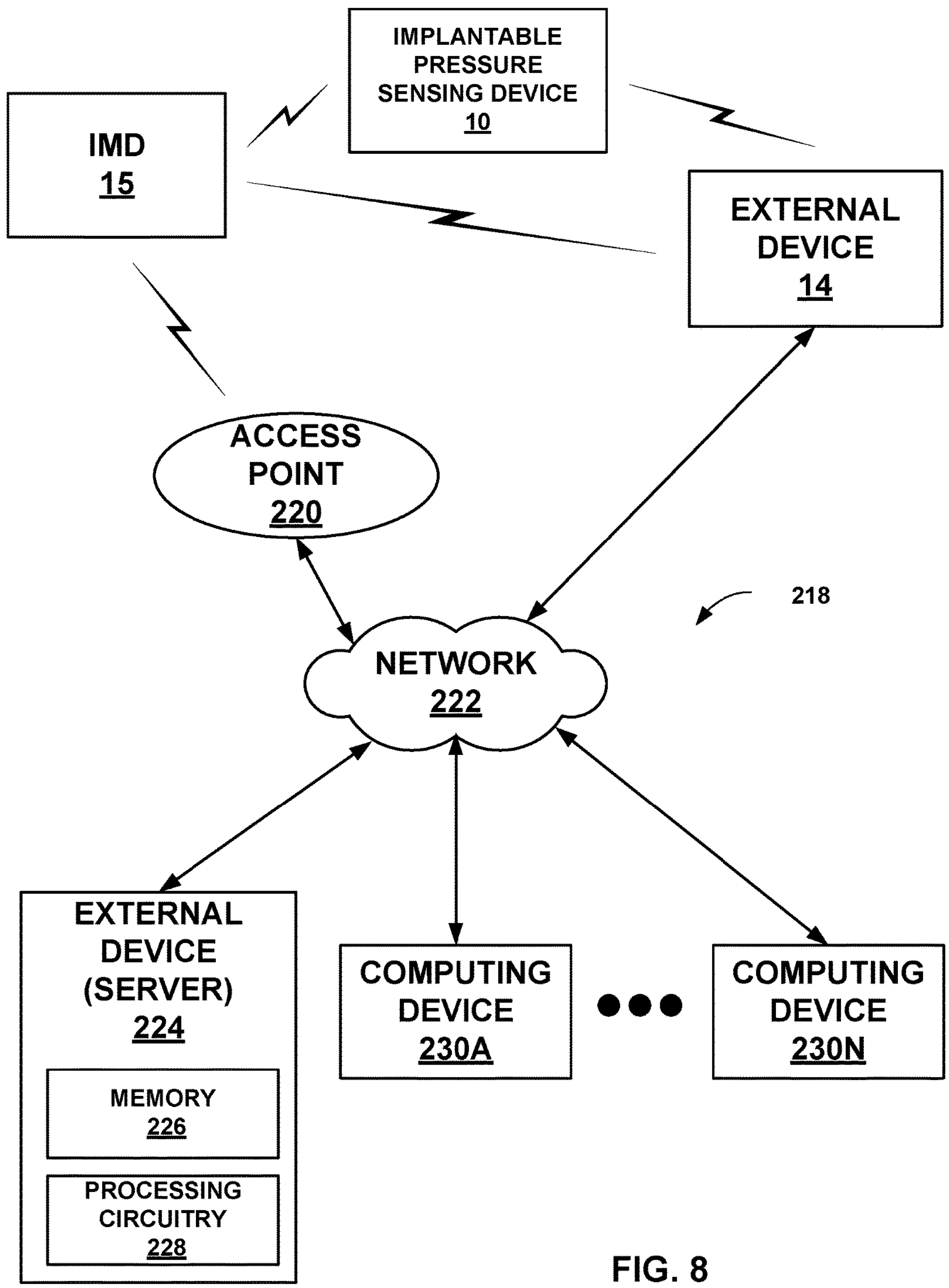
FIG. 8 is a functional block diagram illustrating an example system that includes external computing devices and one or more other computing devices that are coupled to an implanted medical device, sensing devices, and an external device via a network according to various examples described in this disclosure.

FIG. 8 is a functional block diagram illustrating an example system that includes external computing devices, such as a server 224 and one or more other computing devices 230A-230N, that are coupled to IMD 15, pressure sensing device 10, and external device 14 via a network 222. In this example, IMD 15 may use its communication circuitry 168 to, e.g., at different times and/or in different locations or settings, to communicate with external device 14 via a first wireless connection, and to communicate with an access point 220 via a second wireless connection. In the example of FIG. 8, access point 220, external device 14, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate IMD 15, e.g., periodically or in response to a command from the patient or network 222, to retrieve cardiovascular pressure measurements, pressure waveforms, corresponding times of day, corresponding posture data, and/or other operational or patient data from IMD 15. Access point 220 may provide the retrieved data to server 224 via network 222. In various examples, access point 220 may be any example of transceiver 24 described above.

In some cases, server 224 may be configured to provide a secure storage site for data that has been collected from IMD 15, from pressure sensing device 10, and/or from external device 14. In some cases, server 224 may assemble data in web pages or other documents for viewing by trained professionals, such as clinicians, via computing devices 230A-230N. The illustrated system of FIG. 8 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 15 and processing circuitry 200 of external device 14, relating to cardiovascular pressure measurements. In the example of FIG. 8, server 224 includes a memory 226 to store cardiovascular pressure measurements, along with corresponding data such as time of day, posture, heart rate, activity level, and respiration rate, received from IMD 15 and/or external device 14, and processing circuitry 228, which may be configured to provide some or all of the functionality ascribed to processing circuitry 160 of IMD 15 and processing circuitry 200 of pressure sensing device 10 as described herein.

Figure 9:
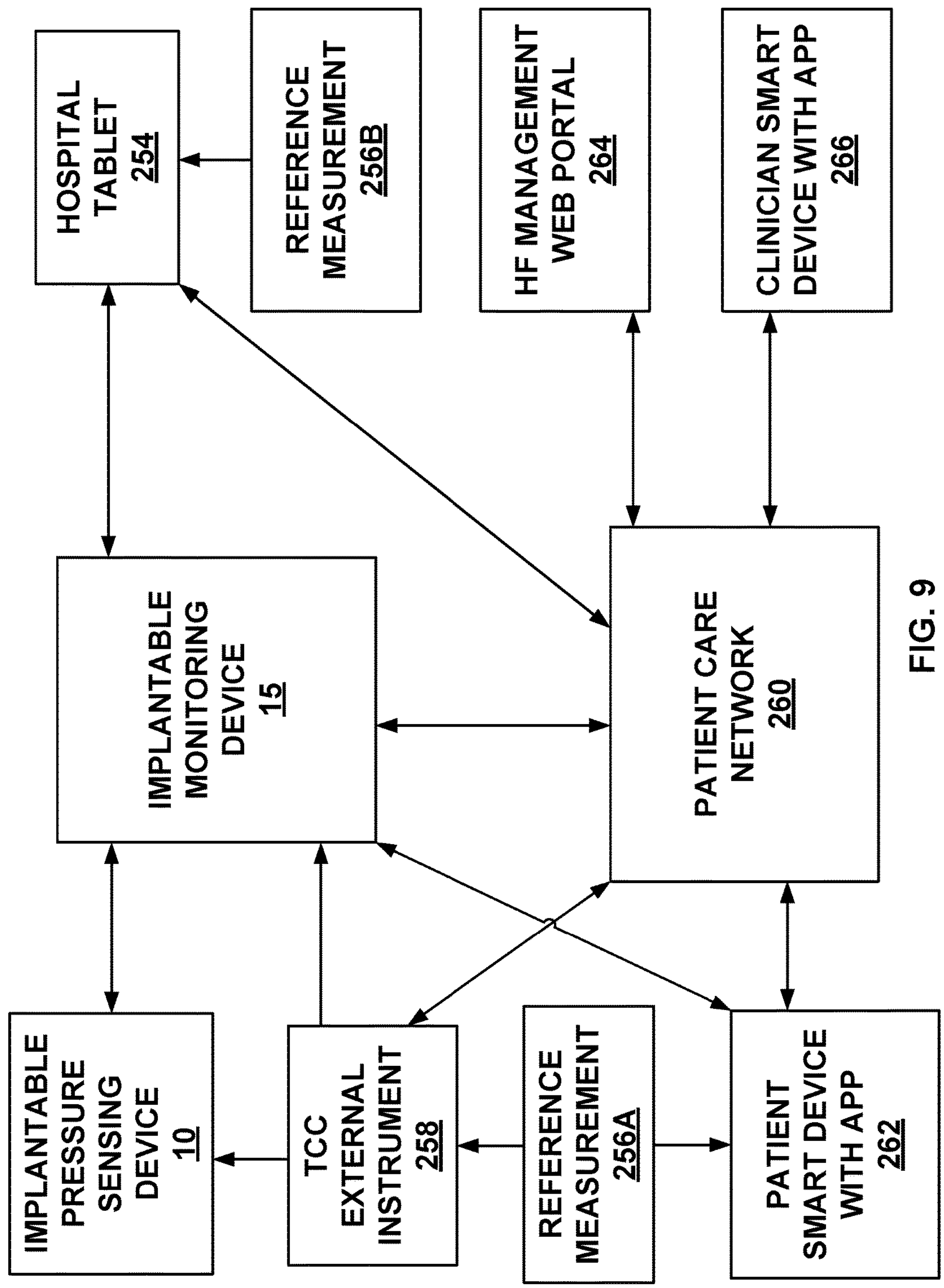
FIG. 9 is a block diagram illustrating an example system that includes external computing devices, an external instrument, a patient smart device, and a clinician smart device according to various examples described in this disclosure.

FIG. 9 is a block diagram illustrating an example system that includes external computing devices, such as hospital tablet 254, TCC external instrument 258, patient smart device 262, clinician smart device 266. Implantable pressure sensing device 10 may correspond to any of the pressure sensing devices 10 and sensor circuits 12 in FIG. 1A, in FIG. 1B, in FIGS. 2A-2B, FIGS. 3A-3B, FIGS. 4A-4B, pressure sensing device 10 in FIG. 8, or another pressure sensing device configured to implement the techniques for measuring cardiovascular pressure as described in this disclosure and the equivalent thereof. Implantable medical device (IMD) 15 may correspond to any of IMD 15A in FIG. 1A, IMD 15B, in FIG. 1B and FIG. 5, IMD 15 in FIG. 6, IMD 15 in FIG. 8, or another IMD configured to implement the techniques for determining whether to store or discard cardiovascular pressure measurements as described in this disclosure, and the equivalents thereof. In the example depicted in FIG. 9, IMD 15 may include communication links with implantable pressure sensing device 10, hospital tablet 254, TCC external instrument 258, patient care network 260, and patient device 262.

The system of FIG. 9 may notify a patient or clinician of a cardiovascular pressure measurement through one or more devices. For example, TCC external instrument 258 may communicate with IMD 15 and/or implantable pressure sensing device 10 via tissue conductive communications (TCC) through the body tissue of the patient. One or both of TCC external instrument 258 and patent smart device 262 may include reference measurement 256A, which may be a measurement of local air pressure to calibrate or adjust the cardiovascular pressure measurements taken by implantable pressure sensing device 10. Although reference measurement 256A is depicted as a single measurement, each of TCC external instrument 258 and patent smart device 262 may include or communicate with a separate reference measurement device.

Hospital tablet 254 and patient care network 260 may communicate with IMD 15 via radio frequency (RF) waves or TCC. Hospital tablet 254 may receive reference measurement 256B, which may be a same or a separate reference measurement device as reference measurement device 256A. A patient or clinician may use hospital tablet 254 or TCC external instrument 258 to obtain measurements and/or determine medication instructions.

Patient care network 260 may include communication links hospital tablet 254, TCC external instrument 258, patient smart device 262, HF management web portal 264, and clinician smart device 266. Patient care network 260 may also include a communication link directly with hospital tablet 254. As a result, a clinician may access a patient's cardiovascular pressure measurements through hospital tablet 254 or clinician smart device 266 when the patient is in the hospital. A clinician may access cardiovascular pressure measurements of a patient through clinician smart device 266 when the patient is not in the hospital if IMD 15 has a remote communication link with patient care network 260. One or more of hospital tablet 254, TCC external instrument 258, patient smart device 262, and clinician smart device 266 may output instructions to a clinician or a patient. In some examples, a device of FIG. 9 may instruct a patient to take blood-pressure medication or medications to treat congestive heart failure based on elevated cardiovascular pressure measurements taken by implantable pressure sensing device 10. A device that displays medication instructions may communicate with patient care network 260 to determine the medication instructions to display to a patient. A device of FIG. 9 may generate an alert to a clinician or patient based on abnormal or unhealthy cardiovascular pressure measurements.

Figure 10A:
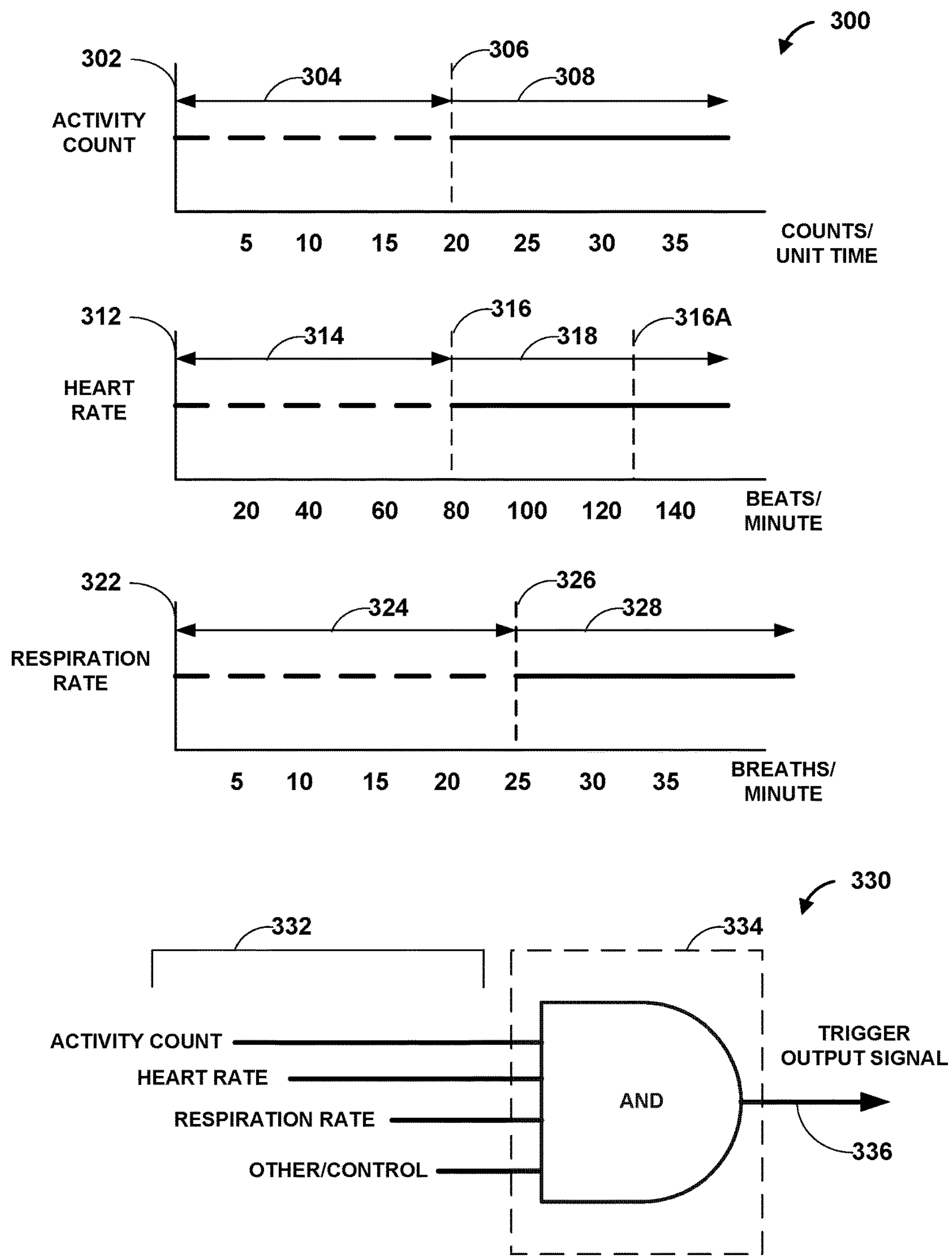
FIG. 10A includes a graphical illustration of example input parameters used to control a trigger circuitry for generation of a trigger output signal according to various examples described in this disclosure.

FIG. 10A includes a graphical illustration 300 of example input parameters used to control trigger circuitry 330 for generation of a trigger output signal. In various examples, trigger circuitry 330 is located in an implantable device, such as IMD 15A (FIG. 1A) or IMD 15B (FIG. 1B and FIG. 5) or IMD 15 (FIG. 6, FIG. 8, and FIG. 9). However, trigger circuitry 330 is not limited to being located in a particular device, and may also be located in a device that is external to a patient, such as external device 14 (FIG. 1A, FIG. 1B, FIG. 8). Graphical illustration 300 includes graphical illustrations of an example input parameter 302 based on an activity count, another example input parameter 312 based on heartrate, and another example input parameter 322 based on respiration rate. Input parameters 302, 312, and 322 in this example all correspond to physiological parameters associated with a patient, i.e., activity count, heartrate, and respiration rate, respectively. However, examples of input parameters are not limited to these physiological parameters of a patient, and may comprise any physiological characteristics of a patient that can be measured, and/or derived from a measured physiological characteristic of a patient. In addition, example input parameters are not limited to physiological characteristic of a patient, and may include parameters based on non-physiological parameters not directly associated with a patient, such as time or calendar dates, or status of a timer, such as a timer that tracks a minimum time from the last time that a trigger output signal was generated (issued) by trigger circuitry 330.

In various examples, the input parameters may correspond directly to, or be based on, sensed physiological parameters of a patient that were provide by one or more sensors included in devices implanted in the patient, and/or sensors external to the patient. For examples, one or more of the input parameters provided to trigger circuitry 330 may be values derived from physiological parameters of a patient that were sensed by sensor circuits 17 or 19 of IMD 15 as shown and described with respect to FIG. 1A and FIG. 1B. In various examples, the input parameters provided to trigger circuitry 330 may be derived from sensed signals sensed by sensor circuit 162 and/or provided by sensors 166 as illustrated and as described above with respect to FIG. 6. Processing circuitry, such as processing circuitry 160 as shown in FIG. 6, may process the sensed signals to generate the values, such as the current values, for one or more of the input parameters. These current values for input parameters may be stored, for example in memory 170 of FIG. 6, and the stored values provided to trigger circuitry 330 either on a continuous basis, or for at some predetermined reoccurring time interval.

As illustrated, each of the input parameters 302, 312, 322 are plotted respectively along a separate horizontal axis, the horizontal axis representative a range of possible numerical values associated with the input parameter 302, 312, 322 being plotted on the respective graphs. Each of the graphs include a representation of a threshold value located at some predefined value along the horizontal axis. For example, the graph of input parameter 302 illustrates numerical values for an activity count associated with a patient, ranging from a value of zero at the origin of the horizontal axis, and increasing to a value of 35 moving to the right along the horizontal axis for the activity counts per some predetermined unit of time, for example activity counts/per minute. A threshold value of 20 activity counts/unit time is illustrated by dashed line 306. Values for the activity count associated with a patient that are in the range from zero to below the threshold value of 20, as illustrated by arrow 304, are represented by a horizontal dashed line in the graph. Any values for the activity count that equals or exceeds a value of 20 are represented by a solid line and arrow 308 for input parameter 302. The status value associated the activity count input parameter 302 of a patient at any given time can be classified by comparison of the current activity count for the patient to the threshold value repressed by the value at dashed line 306, wherein classification of the present or current value of the activity count is below the threshold value (e.g., less than a numerical value of 20 in this example), may be classified as not satisfying the threshold value, and for example can be assigned a status having binary value of "zero." On the other hand, if the numerical value associated the activity count input parameter 302 of a patient at any given time is equal to or exceeds the numerical values of the threshold value (e.g., equal to or greater than a numerical value of 20 in this example), the activity count may be classified as satisfying the threshold value (e.g., current value satisfies threshold value for the parameter), and for example can be assigned a status having a binary value of "one."

The current value for the activity count in some examples is the value calculated for the activity count at the last time the calculation was made. For example, the number of occurrences of a patient activity that is determined to counted as an "activity" for purposes of the activity count is tracked over a given period of time, for example for 30 seconds. At the end of a given 30 second period of time, the total number of activities that were detected during that time period is determines, and the activity count/per unit time is calculated based on the count and the time period during which the activities were counted, and becomes the "current value" for the input parameter 302. In some examples, this current value will be maintained as the value for the activity count input parameter until the next subsequent value for the activity count input parameter is calculated. In some examples, that next subsequent value is calculated at the end of the same time period used to calculate the current value following the end of the time period used to calculate the current value. For example, 30 seconds after ending the time period used to calculate the current value for the activity count, a new current value is calculated based on the number of activity counts that occurred during the 30 second time period immediately following the end of the 30 second time period used to calculate the previous current value.

In a similar manner, the graph of input parameter 312 illustrates numerical values for a heartrate associated with the patient, ranging from a value of zero at the origin of the horizontal axis, and increasing to a value of 140 moving to the right along the horizontal axis for the heartrate. A threshold value of 80 beats/minute is illustrated by dashed line 316. Values for the heartrate associated with a patient that are in a range from zero to below the threshold value 80 beats/minute, as illustrated by arrow 314, are represented by a horizontal dashed line in the graph. Any values for the heartrate that equals or exceeds a value of 80 beats/minute are represented by a solid line and arrow 318 for input parameter 312. The numerical value associated the heartrate of a patient at any given time can be classified by comparison of the current value of the heart rate for the patient to the threshold value repressed by the value at dashed line 316, wherein classification of the present or current value of the heartrate below the threshold value (e.g., less than a numerical value of 80 beats/minute in this example), may be classified as not satisfying (e.g., not exceeding) the threshold value, and for example can be assigned a status having a binary value of "zero." On the other hand, if the numerical value associated the heartrate of a patient at any given time period is equal to or exceeds the numerical values of the threshold value (e.g., equal to or greater than a numerical value of 80 beats/minute in this example), the heart rate may be classified as satisfying (e.g., exceeding) the threshold value (e.g., current value satisfies threshold value for the parameter), and for example can be assigned a status having a binary value of "one."

In some examples, in order for the current value of a physiological parameter to be considered satisfactory, the current value needs to fall within a range of values, for example have a value that exceeds a first threshold valued, but also does not exceed a second threshold value that is different from the first threshold value, By way of illustration, for input parameter 312 related to a patients heartrate, dashed line 316 may be a first threshold level set at a value of 80, and dashed line 316A may be a second, different threshold level set at a value of 130. In this illustrative example, for the current value of the heart rate of the patient to be considered to be "satisfactory" for purposes of providing a positive status for determining whether to triggering pressure sensing, the current value of the heartrate must exceed or be equal to 80, but must not exceed a value of 130. If the current value of the heartrate falls within or is equal to these threshold values, the current value may be considered to satisfy the threshold requirement for input parameter 312, and may be assigned a positive status value, for example a status having a binary value of "one". On the other hand, if the current value of the heartrate is less than 80 or is greater than 130, the current value for the heartrate is not considered to satisfy the threshold requirements for this input parameter, and may be assigned a non-positive status, for example a status having a binary value of "zero" Use of a threshold range for a particular input parameter may allow for a required minimum value to be achieved by the current value for the input parameter, but to also disqualify any current value for the input parameter that is considered for example to be too high, and therefore may be suspect as a value measure of the current value, or may be associated with some other issues, such as a heart related issue in the patient, that is determined to disqualify the patient's status from triggering a pressure sensing operation with respect to the patient under these conditions. The use of a range of threshold values having more than one defined threshold limit determine a status associated with a current value for the input parameter is not limited to heartrate or to any particular input parameter, and may or may be applied to any given one of the input parameters on a parameter-by-parameter basis.

The current value for the heartrate in some examples is the value calculated for the patient's heart rate at the last time the calculation was made. For example, the number of heart beats a patient may be detected and counted over a predefined period of time, for example 10 seconds, for purposes of calculating a current value of the patient's heart rate. At the end of a given 10 second period of time, the total number of heartbeats that were detected during that time period is determined, and the heartrate/per unit time is calculated based on the number of heartbeats detected over the predefined time period during with the heartbeats were counted, and becomes the "current value" of the input parameter 312. In some examples, this current value will be maintained as the value for the patient's heartrate until the next subsequent value for the heartrate is calculated. In some examples, that next subsequent value for the heartrate is calculated at the end of the same time period used to calculate the current value following the end of the time period uses to calculate the current value, for example 10 seconds after ending the time period used to calculate the current vale for the heart rate, a new current value is calculated based on the number of heartbeats that occurred during the 10 second time period immediately following the previous 10 second time period used to calculate the current value for the patient's heartrate.

In a similar manner, the graph of input parameter 322 illustrates numerical values for a respiration rate associated with the patient, ranging from a value of zero at the origin of the horizontal axis, and increasing to a value of 35 breaths/minute moving to the right along the horizontal axis for the heart rate. A threshold value of 25 breaths/minute is illustrated by dashed line 326. Values for the respiration rate associated with a patient that are in a range from zero to below the threshold value 25 breaths/minute, as illustrated by arrow 324, are represented by a horizontal dashed line in the graph. Any values for the respiration rate that equals or exceeds a value of 25 beats/minute are represented by a solid line and arrow 328 for input parameter 322. The numerical value associated the respiration rate of a patient at any given time can be classified by comparison of the current value of the heart rate for the patient to the threshold value repressed by the value at dashed line 326, wherein classification of the present or current value of the respiration rate below the threshold value (e.g., less than a numerical value of 25 breaths/minute in this example), may be classified as not satisfying (e.g., not exceeding) the threshold value, and for example can be assigned a status having a binary value of "zero." On the other hand, if the numerical value associated the respiration rate of a patient at any given time is equal to or exceeds the numerical values of the threshold value (e.g., equal to or greater than a numerical value of 25 breaths/minute in this example), the respiration rate may be classified as satisfying (e.g., exceeding) the threshold value (e.g., current value satisfies threshold value for the parameter), and for example can be assigned a status having a binary value of "one."

The current value for the respiration rate in some examples is the value calculated for the patient's respiration rate at the last time the calculation was made. For example, the number of breaths a patient took may be detected and counted over a predefined period of time, for example 30 seconds, for purposes of calculating a current value of the patient's respiration rate. At the end of a given 30 second period of time, the total number of breaths that were detected during that time period is determined, and the respiration rate in breaths/per unit time is calculated based on the number of breaths detected over the predefined time period during with the breaths taken were counted, and becomes the "current value" for the input parameter 322. In some examples, this current value will be maintained as the value for the patient's respiration rate until the next sequential value for the respiration rate is calculated. In some examples, that next sequential value for the patient's respiration rate is calculated at the end of the same time period used to calculate the current value following the end of the time period uses to calculate the current value, for example 30 seconds after ending the time period used to calculate the current vale for the respiration rate, a new current value is calculated based on the number of breaths that occurred during the 30 second time period immediately following the previous 30 second time period used to calculate the current value for the patient's respiration rate.

In some examples, the classifications of each of the current values of the input parameters is provided as a separate input, represented as some of the inputs 332, that are provided to the logic circuit 334 of trigger circuitry 330. As illustrated, logic circuit 334 includes a separate input for the activity count input parameter 302, the heartrate input parameter 312, and the respiration rate input parameter 322. In addition, logic circuit 334 may includes one or more additional separate inputs, represented by the "other/control" input. In various examples, logic circuit 334 is configured to receive each of the inputs 332, and based at least in part on the status of these inputs provided by inputs 332, to determine whether to provide a trigger output signal at output 336. In various examples, when logic circuit 334 provides the trigger output signal at output 336, the trigger output signal is provided to additional circuits, such as processing circuitry 160 and/or communication circuitry 168 as shown in FIG. 6, to trigger an event causing a measurement, or a sequence of measurements of the patient's pulmonary blood pressure, as described in this disclosure, to occur.

The logical functions performed by logic circuit 334 are not limited to any particular logic function or to any particular type of logic. By way of example, as noted above a current status for each of the input parameters 302, 312, 322 may be classified using a status having a binary value of "zero" or "one" based on a comparison to the current value to a threshold value or a threshold range of values assigned to that input parameter. These binary values may be provided to the inputs 332, respectively for each of the activity count, heartrate, and respiration rate inputs. These statuses as assigned to these input parameters, along with the status of the other/control input(s), may be logically ANDed together by logic circuit 334, and if all inputs provide an input value of "one" or a positive input status, logic circuit 334 is configured to provide the trigger output signal, for example a logical value of "one," at the output 336. The presence of the trigger output signal (e.g., the logical "one") at output 336 is then configured to trigger the process of taking measurements of the patient's pulmonary blood pressure. In various examples, the status of the other/control line is set based on an enable/disable flag stored in a memory register of the implanted medical device, and may be set based on instructions received from an external device, such as external device 14, and transmitted to the implanted medical device. In some examples, the status provided at the other/control line is provided by a timer, the duration of the time set by a user, for example a physician, to control the frequency (time interval) between the triggering of the sensing events (for example once per day, once per week, once per month).

The status of the other/control line of the inputs 332 may be used to further regulate when logic circuit 334 in fact provides the trigger output signal. For example, a minimum time period between when the last trigger output signal was provided at output 366 and when another trigger output signal is allowed to be issued at output 336 may be defined. In some examples, the issuance of the trigger output signal may be limited to no more than one occurrence within a given 24-hour period. As such, once a trigger output signal has been issued by trigger circuitry 330, the other/control input may be held in a status, such as providing a binary value of "zero," for the predefined time period following issuance of a trigger output signal. By providing a status value of "zero" over the predefined time period, the other/control line will prevent trigger circuitry 330 from issuing another trigger output signal during the predefined time period, regardless of the status of the other input parameters at inputs 332. Once the predefined period has elapsed, the status provided by the other/control line may be changed to a status of "one," thereby allowing trigger circuitry 330 to issue another trigger output signal when the statuses provided on each of the additional input parameter at inputs 332 also provide a positive input status. By controlling the status provided on the other/control line, the ability of trigger circuitry 330 to generate a trigger output signal at output 336 may be regulated or otherwise controlled.

In various examples, the statuses assigned to each of input parameters 302, 312, 322 may be provided at inputs 332 continuously, and the regulation of the logic circuit 334 provided by the other/control line. In other examples, the input statuses associated with the current values of input parameters 302, 312, 322 may only be provided to inputs 332 at certain times, for example based on periodic polling of these statuses. Polling this the status of current values of the input parameters 302, 312, 322 may be based on a predetermined polling rate, such as polling the input parameters every so many seconds, such as every 1 second, or every 10 seconds or a polling rate somewhere between 1 and 10 seconds. In some examples, polling rates used for pooling the status of the input parameters is greater than 10 seconds, for example using a polling rate of one or more minutes. In various examples, the status of input parameters 322 is only applied to inputs 332 for a predetermined period of time, for example for 100 milliseconds, during which time the logic circuit 334 received these inputs and determines whether or not to provide the trigger output signal. Once the predefined time period has elapsed, (e.g., the 100 millisecond time period has elapsed) the statuses of the input parameters 302, 312, 322 are removed from the inputs 332, and trigger circuitry 330 is configured so that trigger circuitry 330 will not provide a trigger output signal at output 366 until the statuses at the inputs 332 is again provided at inputs 332. The time for providing the status of input parameters 322 to inputs 332 is not limited to 100 milliseconds or any particular time period, and may be provided for a time period of less than 100 milliseconds, or a time period longer than 100 milliseconds before the status of inputs 322 is removed from inputs 332.

Figure 10B:
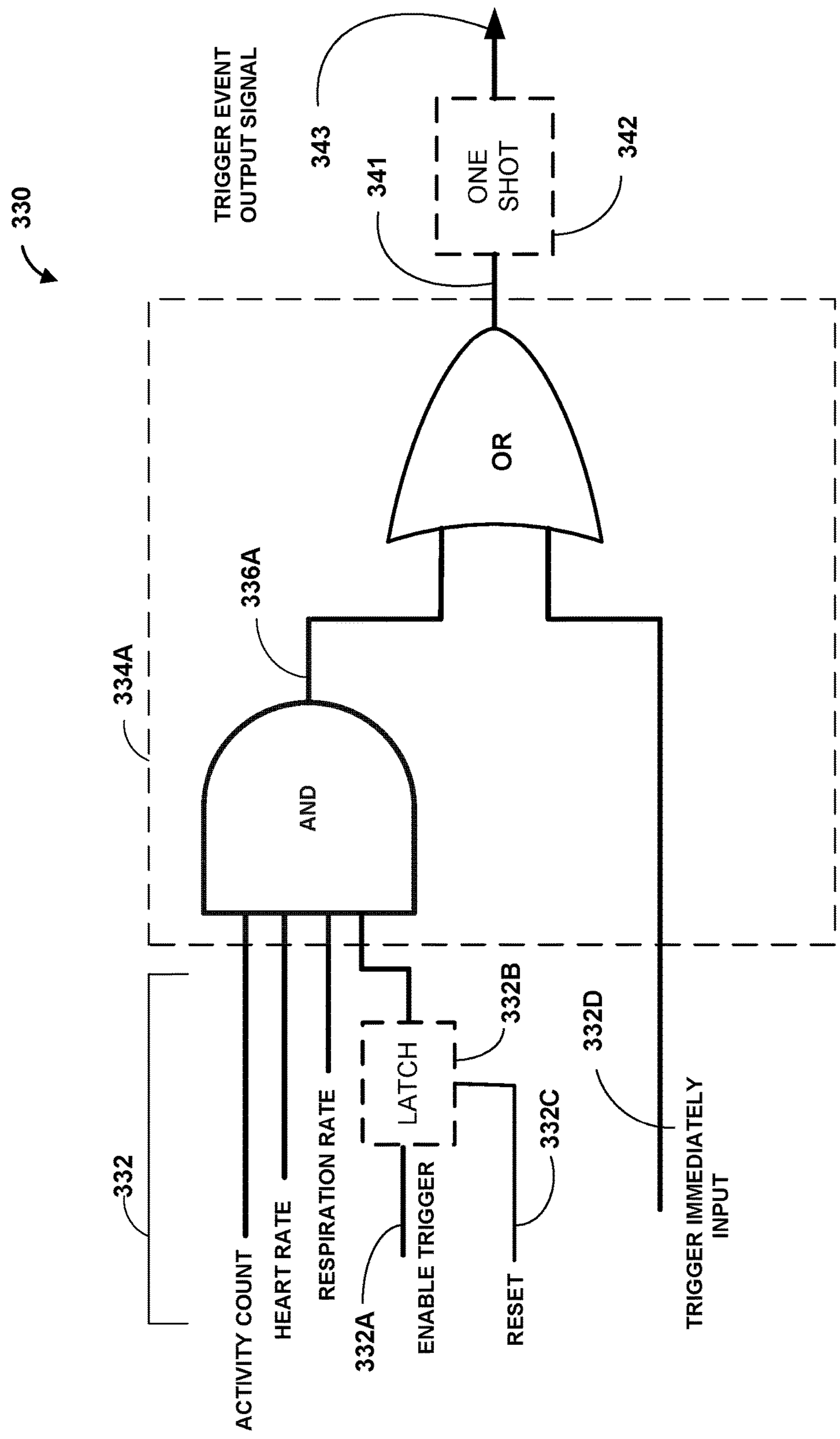
FIG. 10B includes a graphical illustration of example input parameters used to control a trigger circuitry for generation of a trigger output signal according to various examples described in this disclosure.

FIG. 10B includes a graphical illustration of example input parameters used to control another example of trigger circuitry 330 for generation of a trigger output signal. In various examples, trigger circuitry 330 as illustrated in FIG. 10B is located in an implantable device, such as IMD 15A (FIG. 1A) or IMD 15B (FIG. 1B and FIG. 5) or IMD 15 (FIG. 6, FIG. 8, and FIG. 9). However, trigger circuitry 330 is not limited to being located in a particular device, and may also be located in a device that is external to a patient, such as external device 14A (FIG. 1A, FIG. 8) or in external device 14B (FIG. 1B). Trigger circuitry 300 may be implemented by or as part of processing circuitry, such as but not limited to processing circuitry 160 shown in FIG. 6 and/or processing circuitry 228 shown in FIG. 8. In FIG. 10B, the graphical illustration of trigger circuitry 330 includes a graphical illustration of an example input parameter provided at inputs 332 based on an activity count, another example input parameter based on heart rate, and another example input parameter based on respiration rate. As described above with respect to input parameters 302, 312, and 322 in FIG. 10A, input parameter statuses provided at inputs 332 in FIG. 10B may provide a status, such as a binary "one" or a "zero" value, that is provided as an input to the logical AND of logic circuit 334A.

In addition, input parameters provided at inputs 332 include an enable trigger input 332A that is, in some examples, coupled to latch 332B, or may be directly coupled to the inputs of the AND circuit of logic circuit 334A in other examples. If latch 332B is included, the enable trigger input 332A is coupled to the input of latch 332B, and when a positive value is provided at enable trigger input 332A, latch 332B is latched to provide a positive output from the latch 332B and to the inputs of the logical AND of logic circuit 334A. Latch 332B may also include a reset line 332C coupled to the latch, the reset line 332C configured to provide a signal that resets latch 332B to a non-positive output to the logical AND circuit of logic circuit 334A. The status provided by the enable trigger input 332A may be used to allow triggering of the trigger output signal to be enabled and disabled. When the status of the enable trigger input 332A is positive, or has latched the latch 332B to provide a positive input to the logical AND of logic circuit 334A, then trigger circuitry 330 is enabled to provide a trigger output signal whenever the additional input parameters provided at inputs 332 also all provide a positive status. On the other hand, if the enable trigger input 332A is not providing a positive input status, or the latch 332B has been unlatched by activation of the reset line 332C, and is not providing a positive signal to the logical AND, then at least the output 336A of the logical AND of logic circuit 334A cannot provide positive output, and thus prevents AND portion of logic circuit 334A from triggering the generation of the trigger output signal. The status of the enable trigger input 332A may be determined by a status of a memory register stored in memory 170 of IMD 15. The status of this memory register can be set based on input information received at IMD 15 from an external device, such as external device 14A. By controlling the status of enable trigger input 332A and/or latch 332B, the automatic triggering of a sensor assembly to take pulmonary blood pressure measurements passed on the status of the input parameters associated with activity count, heartrate, and respiration rate can be enable or disabled.

In addition, as shown in FIG. 10B logic circuit 334A includes a logical "OR" that has a first input coupled to the output 336A of the logical AND, and a second input coupled directly to a trigger immediately input 332D. The trigger immediately input 332D may provide a positive status at the input to the logical OR when IMD 15 receives a signal from an external device, such as external device 14 or transceiver 24, requesting that a sensor assembly, such as pressure sensing device 10, be triggered to perform pressure sensing measurements upon receipt of the request to immediately sense pressures. Thus, the logical OR function of logic circuit 334A is configured to generate a trigger output signal at output 341 when the input parameters provided at inputs 332 provide positive inputs statuses to the logical AND, or to also provide the trigger output signal when a positive status is provided at the trigger immediately input 332D, regardless of the status of the parameter inputs provided at inputs 332 associated with activity count, heart rate, respiration rate, and in some examples the enable trigger status.

In some examples, the output 341 is configured to provide the trigger output signal when generated as an output from the OR function. In some examples, output 341 is coupled to a one-shot 342, the output 343 of the one-shot configured to provide a pulse signal, for some predetermined time period, when the trigger output signal is generated at the output 341. The output 343 from one-shot 342 may then be utilized as the trigger output signal to send to the sensor assembly, such as pressure sensing device 10, that then takes the requested pressure sensor measurements. The use of the one-shot 342 to pulse the trigger output signal may prevent an unintended re-triggering of the pressure sensing due to inadvertently leaving the trigger output signal in an "ON" or an output state that indicates a request to trigger pressure sensing.

Input parameters 302, 312, and 322 in this example all correspond to physiological parameters associated with a patient, i.e., activity count, heart rate, and respiration rate, respectively, of a patient. However, examples of input parameters are not limited to these physiological parameters of a patient, and may comprise any physiological characteristics of a patient that can be measured, and/or derived from a measured physiological characteristic of a patient. In addition, example input parameters are not limited to physiological characteristic of a patient, and may include parameters based on non-physiological parameters not directly associated with a patient, such as time or calendar dates, or status of a timer, such as a timer that tracks a minimum time from that a last time that an output signal was triggered (issued) by trigger circuitry 330.

Figure 11:
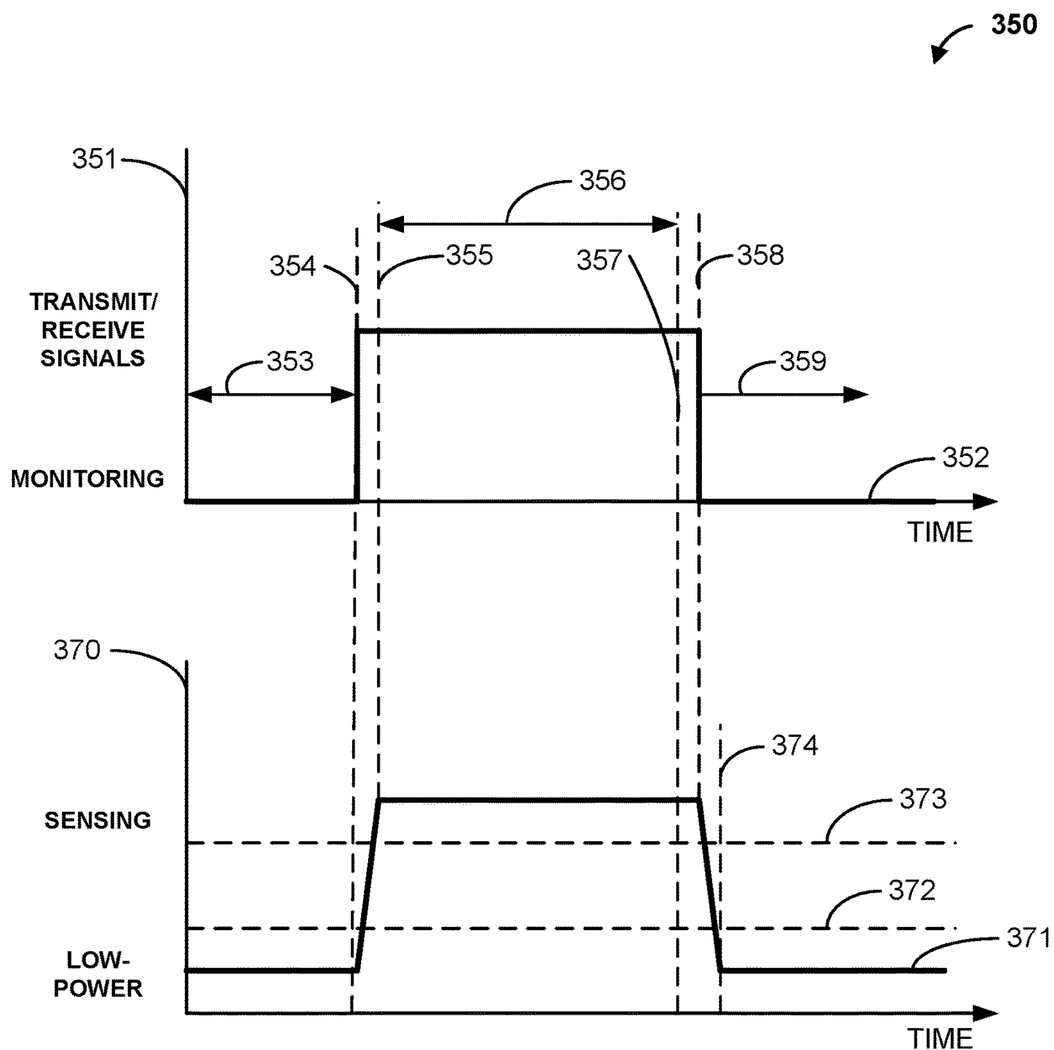
FIG. 11 includes a graphical illustration of example states for a monitoring device and a sensing device in accordance with various techniques described in the disclosure.

FIG. 11 includes a graphical illustration 350 of example states for a monitoring device and a sensing device in accordance with various techniques described in the disclosure. Graphical illustration 350 includes a first graph 351 illustrating different states that an IMD 15, such as IMD 15A (FIG. 1A), IMD 15B (FIG. 1B and FIG. 5), IMD 15 (FIG. 6, FIG. 8, and FIG. 9) may reside in. The IMD 15 having states as depicted in first graph 351 is not limited to any particular device, and may be any device or devices that are configured to monitor input parameters that may be used as a basis for determining if a triggering event has occurred the would trigger the outputting of a trigger output signal. As illustrated in first graph 351, the IMD 15 can transition from a monitoring state to a transmit/receive signals state, and back to the monitoring state over time, as depicted by trace 352. Trace 352 initially resides in a monitoring state, as depicted by the time period represented by arrow 353. During the time period 353, the monitoring device may continuously, or at some predetermined sampling rate, monitor the current values and/or a categorized status values, as previously described, that are assigned to a set of input parameters being used to determine if a trigger event has occurred. IMD 15 may also monitor the status of additional inputs, such as a status of a timer that is used to determine if a minimum amount of time has elapsed between the present and the time a last trigger event occurred and a trigger output signal was issued. During the time period 353, IMD 15 determines that a triggering event has not occurred, and/or that the minimum amount of time has not elapsed since the occurrence of the last triggering event, and thus remains in the monitoring mode.

Graphical illustration 350 also includes a second graph 370 illustrating different states that an implantable pressure sensing device 10, (herein after "pressure sensing device 10") such as pressure sensing device 10A (FIG. 1A), pressure sensing device 10B (FIG. 1B), or implantable pressure sensing device 10 (FIG. 2A-2B, FIG. 3A-#B, FIGS. 4A-4B, FIG. 7-9) may reside in. As shown in second graph 370, pressure sensing device 10 may reside in a low power mode wherein the power level being used by the pressure sensing device 10, represented by trace 371, is below a threshold power level represented by dashed line 372. When the pressure sensing device 10 is operating at power levels below the threshold power level, the pressure sensing device 10 may be considered to be in sleep mode, or a low-power mode configured to conserve the battery power or other on-board power source(s) provided to power the operations of the pressure sensing device 10. The time line illustrated for second graph 370 corresponds to a same time line illustrated in first graph 351. During the time period 353, the pressure sensing device 10 has not detected that a triggering event has occurred, and thus the pressure sensing device 10 remains in the low-power state during time period 353.

At a time indicated by dashed line 354, IMD 15 detects that a triggering event has occurred. At time 354, IMD 15 transitions for the monitoring state to the transmit/receive signals state, as indicated by the rise in the level of trace 352 shown in first graph 351 at time 354. Once in the transmit/receive signal mode, IMD 15 is configured to generate a trigger output signal, as described above, indicating that a triggering event has occurred, and to transmit to the pressure sensing device 10 the trigger output signal, for example as a voltage pulse. When the trigger output signal is received by the pressure sensing device 10, pressure sensing device 10 begins to transition from the low-power mode to the sensing mode, as represented by the transition of trace 371 between time 354 and ending at time 355. At time 355, the pressure sensing device 10 is in the sensing state, as illustrated by trace 371 being at a level above dashed line 373. At time 355, pressure sensing device 10 begins sensing pressure levels of the blood pressure within the pulmonary artery of the patient where the pressure sensing device 10 is located. In various examples, the implantable pressure sensor associated with pressure sensing device 10 takes pressures measurements over a window of time defined by predetermined length of time, for example between time 355 and time 357, as illustrated by the time period (window) represented by arrow 356 in first graph 351. In various examples, pressure sensing device 10 may begin to transmit data related to one or more of the sensed pressure measurements at any time after time 355. As such, IMD 15 is configured to receive these data transmission signals and the corresponding data transmitted from pressure sensing device 10 during time period 356.

In some examples, pressure sensing device 10 is configured to accumulate data associated with the pressures measured during time period 356, and not to begin transmission of the data corresponding to the pressure measurement until after the completion of sensing of the pressure measurements at end of time period 356. In these examples, pressure sensing device 10 may accumulate the data related to the pressure measurements, and to transmit the signals including the data after time period 356 ends, for example during the time period between time 357 and time 358. During the time period between time 357 and time 358, the IMD 15 remains in the transmit/receive signal mode, and receives the signal transmitted by pressure sensing device 10 that include the data corresponding to the pressure measures taken during time period 356. In some examples, at time 358, pressure sensing device 10 is configured to transmit a signal to IMD 15 indicating that all data related to the pressure sensing measurements taken during the predefined time period 356 have been transmitted as an output from pressure sensing device 10. At time 358, pressure sensing device 10 begins a transition back to the low-power mode over the time period between time 358 and 374. At time 374, pressure sensing device 10 has returned to the low-power mode, as illustrated by the decrease in the level illustrated for trace 371 to a level below threshold level 372. Once in the low-power mode illustrated by trace 371 at time 374, pressure sensing device 10 may remain in the low-power mode until again receiving a triggering signal from IMD 15 indicating that another triggering event has occurred.

Further, at time 358, IMD 15 has received an indication from pressure sensing device 10 that all of the data related to the pressure measurements taking during the predefined time window 356 have now been transmitted to IMD 15, and IMD 15 returns to the monitoring mode following time period 358, as indicated by arrow 359 in first graph 351. Once returned to the monitoring mode, in addition to again monitoring the input parameters and other signals with respect to determining if a triggering event has again occurred, IMD 15 may perform additional functions. These additional functions may comprise transmitting the data received from pressure sensing device 10 to other devices, such as external device 14, or other external devices coupled to a network such as network 222 (FIG. 8). In addition to or instead of transmitting the data, IMD 15 may process the data to generated one or more additional parameter measurable directly from the data or derived from the data. In various examples, the further processing of the data may include processing of the data to provide information corresponding to the data that may be displayed, for example in graphical or tabular format, for visual inspection and analysis by a user. In some examples, further processing of the data by the monitoring device includes such processes as providing curve fitting to sets of data samples corresponding to the pressure sensor measurements.

In various examples, IMD 15 is configured to continue to monitor the input parameter during the entirety of time period 356 while the pressure measurements are being taken. In some examples, if the status of the input parameters does not remain at the same levels and/or statuses that were initially required to trigger the trigger output signal, IMD 15 will discard all of the data associated with the pressure measurements taken during time period 356. In other examples, once the trigger output signal has been transmitted, IMD 15 will receive and retain the data corresponding to the pressure measurement taking during time period 356 regardless of any changes to the status(es) on the input parameters used to initially trigger the pressure sensing. In such examples, the data collected from monitoring the input parameters during the time period 356 while the pressure measurements are being taken will be saved and provided along with and as data corresponding to the pressure sensor measurements regardless of whether or not the status of the input parameters remains at the same levels and/or status that were initially required to trigger the trigger output signal.

Figure 12A:
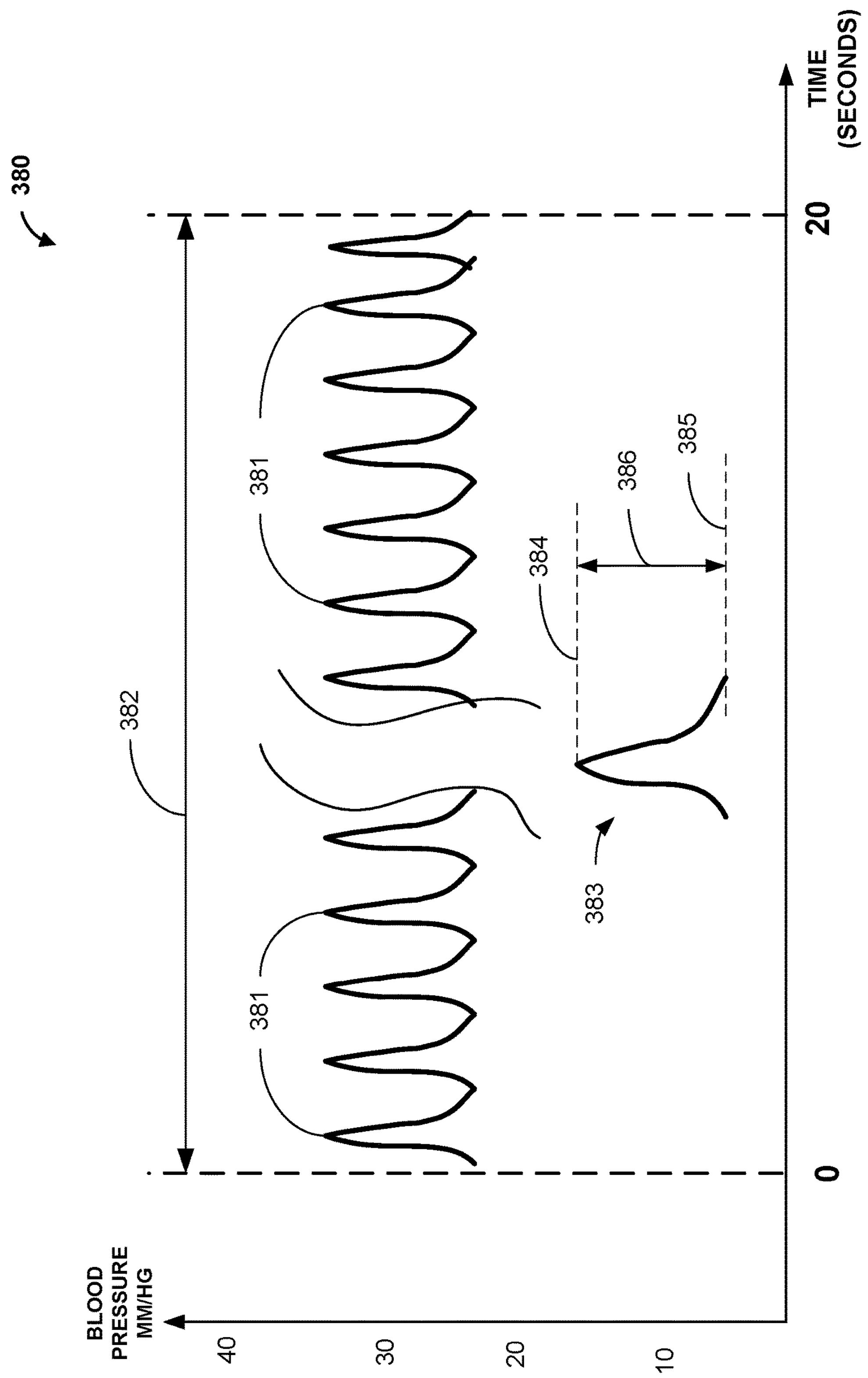
FIG. 12A includes a graphical illustration of illustrative waveforms of pulmonary blood pressures according to various techniques described in this disclosure.

FIG. 12A includes a graphical illustration 380 of illustrative waveforms of pulmonary blood pressures according to various techniques described in this disclosure. Graphical illustration 380 includes illustrative waveforms 381 representative of pulmonary blood pressure measurements (plotted against vertical axis in mm HG) that could be sensed over a predetermined window of time 382. Waveforms 381 are not indicative of actual sensed pulmonary blood pressure measurements, and are not necessary to scale with respect to time. Waveforms 381 are intended to be illustrative of data, sensed for example by a pressure sensing device 10A, of pulmonary blood pressure in a patient. As illustrated, the time window over which the illustrated pressure measurements would be taken is 20 seconds. The data corresponding to waveforms 381 is representative of data that, after being sensed by the sensor assembly, could be processed to provide the graphical illustration similar to that of graphical illustration 380. This graphical illustration is one example of data that could be transmitted to an external device for display by the external device, such as external device 14A and display 14D as illustrated in FIG. 1A.

Based on the trend of values indicated by waveforms 381, various parameters may be determined, e.g., by values measured directly from the waveform and/or by values derived or calculated form the values measured directly from the waveform. For example, illustrative waveform 383 represents pulmonary blood pressures associated with one cycle (one heartbeat), and include a peak (systolic) pressure 384, a low (diastolic) pressure 385, and a difference, represented by arrow 386, between the peak and the low pressure for that cycle. These parameters may be measured for each of the cycles of waveforms 381, and transmitted as data corresponding to the pulmonary blood pressure measurements associated with the sensing performed during the time period 382. One of ordinary skill in the art would understand that many other parameters may be measured from and/or derived from the data illustrated by waveforms 381, and measurements and derivation of any such parameters are contemplated by this disclosure. In addition, the parameters measured and or derived from each of the waveforms may be utilized to develop overall parameters associated with these waveform corresponding to the entirety of the time period 382, such as an average value, a mean value, and median value, or any other type of value that can be derived from a parameter measured from or derived from each individual cycle of the waveform. Any of this data may also processed to be presented in graphical or other forms of information, such as data provided in a tabular format, e.g., illustrating a trend, and that can be provided to external devices for display and for purposes of further analysis. In various examples, the data associated with waveforms 381 may correspond to pressure measurements taken by sensor (s), such as sensors 206, which provide electrical output signals that may be further processed by sensing circuitry 202 and processing circuitry 200 of the pressure sensing device 10 as illustrated and describe above with respect to FIG. 7, to generate the data represented as waveforms 381.

Figure 12B:
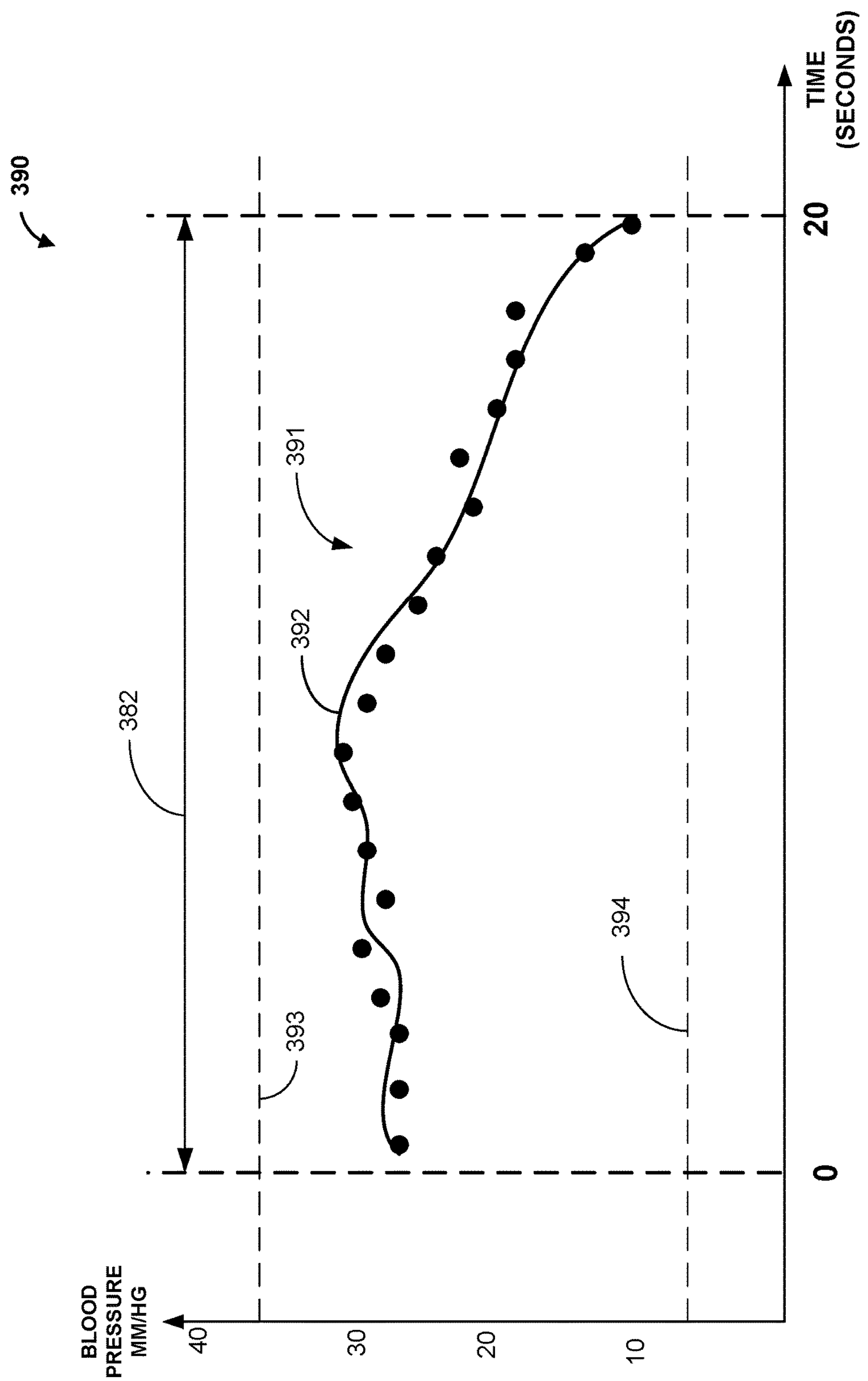
FIG. 12B includes a graphical illustration of a plot of illustrative data that may be derived by processing a waveform of sensed of pulmonary blood pressures according to various techniques described in this disclosure.

FIG. 12B includes a graphical illustration 390 of a plot of illustrative data that could be derived by processing a waveform of sensed of pulmonary blood pressures according to various techniques described in this disclosure. Graphical illustration 390 includes illustrative plot of mean averages, generally indicated by dots 391, calculated for a series of waveforms representative of pulmonary blood pressure measurements (plotted against the vertical axis in mm HG) that could be sense over the predetermined window of time 382. An illustrative trace 392 shows one possible line fitted to the plot of the dots, as would be understood by one of ordinary skill in the art with respect to fitting a line to a set of data points. The dots 391 as illustrated in FIG. 12B are not indicative of actual sensed pulmonary blood pressure measurements, and are not necessary to scale with respect to time. Dots 391 and trace 392 are intended to be illustrative of representative data corresponding to waveforms that could correspond to data of pulmonary blood pressures measured in a patient.

As illustrated, the time window over which the illustrated dots 391 are plotted would be taken is 20 seconds. The dots 391 are representative of data that, after being sensed by the sensor assembly, could have been derived by processing the data to provide the graphical illustration similar to that of graphical illustration 390. Various threshold values, represented by dashed line 393 and 394, may be provided in graphical illustration 390 to aid in the analysis of the data depicted in the graph. For example, the threshold values can be set at levels that if exceeded by any of dots 391, either by being above threshold line 393 or by being below threshold line 394, indicate a condition that might be a serious or an undesirable condition with respect to the patient, and therefore are indicated as such on the graph by being outside the threshold lines. This graphical illustration 390 is one example of data corresponded to measured or derived data points that could be transmitted to an external device for display by the external device, such as external device 14A and display 14D as illustrated in FIG. 1A. In various examples, the data associated with dots 391 may correspond to pressure measurements taken by sensor(s), such as sensors 206, which provide electrical output signals that may be further processed by sensing circuitry 202 and/or by processing circuitry 200 of the pressure sensing device 10 as illustrated and describe above with respect to FIG. 7, to generate the data represented as dots 391.

Figure 13:
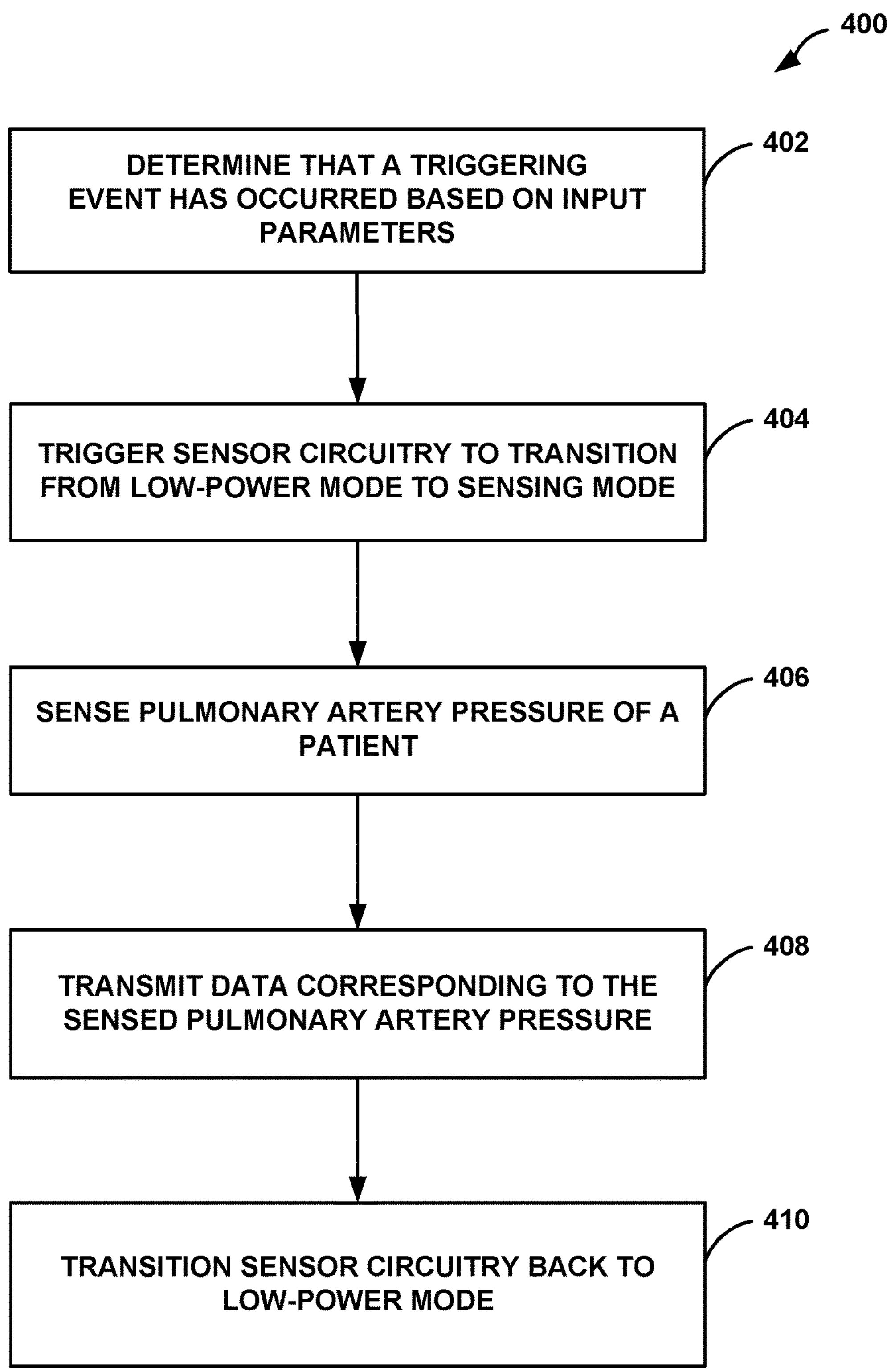
FIG. 13 illustrates a flowchart of a method according to various examples described in this disclosure.

FIG. 13 illustrates a flowchart of a method 400 according to various examples described in this disclosure. Although method 400 is described as being performed by IMD 15B and pressure sensing device 10B as illustrated and described with respect to FIG. 1B, method 400 is not limited to being performed by any particular device or devices, and may be performed by any device or devices configured to perform the functions of method 400, including devices and systems as otherwise described herein. According to method 400, IMD 15B monitors various input parameters, and determines that a triggering event has occurred based on current values, statuses, or some other derived parameter(s) based on monitoring the input parameters (block 402). In various examples, IMD 15B determines, using trigger circuitry 330, that a triggering event has occurred when the status of the input parameters, when logically ANDed together, results in a positive output based on the ANDed inputs. In various examples, the input parameters include a status associated with an activity count, a heartrate, and a respiratory rate of the patient. In various examples, trigger circuitry 330 receives additional information, such as the status of an enable/disable register in a memory 170, as an additional input parameter that is logically ANDed to determine if a triggering event has occurred. In various examples, trigger circuitry 330 receives a status of a timer indicative of whether or not a minimum time period has elapsed since the last issuance of a trigger output signal, the status of the output timer provided as one of the input parameters the is logically ANDed to determine if a trigger event has occurred.

If IMD 15B determines that a triggering event has not occurred, trigger circuitry 330 of IMD 15B does not generated a trigger output signal, and continues to monitor the input parameters, in some examples as some predetermined polling rate. If IMD 15B determines based on monitoring the input parameters that a triggering event has occurred, IMD 15B is configured to trigger an implantable pressure sensing device implanted in a vessel of the patient to transition from a low-power mode to a sensing mode (block 404). Triggering the pressure sensing device includes generating, by the trigger circuitry 330, a trigger output signal. The trigger output signal is then wirelessly transmitted from the IMD 15B, for example via communication circuitry 168, to pressure sensing device 10B, and is received for example by communication circuitry 208 included within pressure sensing device 10B. Once pressure sensing device 10B has received the trigger output signal, sensor assembly transitions from the low-power mode to a sensing mode, and begins sensing pulmonary blood pressure measurements, using for example sensor components 42 of the sensor circuit 12A (block 406). In various examples, pressure sensing device 10B is configured to take pulmonary pressure sensor measurement, either continuously or at some predefined sample rate, for a period of time window having a predefined length of time. In various examples, the predefined sample rate is for taking pulmonary pressure sensor measurements is about 64 Hz. In another example, the predefined sample rate is about 128 Hz. In still another example, the predefined sample rate is about 256 Hz. The predefined sample rate is not limited to these sample rates, and in various examples may be a sample rate in a range of 50 to 300 Hz. In various examples, a length to the time window over which the pulmonary pressure sensor measurements are taken, either continuously or at some predefined sample rate, is defined to have a length of twenty seconds. The length of the time window over which the pulmonary pressure sensor measurements are taken is not limited to being a time period of twenty seconds, or to any particular length of time. In various examples, the length of the time window is more or less than a twenty second length of time. In various examples, the length of the time window over which the pulmonary pressure sensor measurements are taken is in a range of ten seconds to one minute. In various examples, the sensed pulmonary blood pressure measurements may be processed by processing circuitry including in pressure sensing device 10B, such as processing circuitry 200, and stored in a memory on-board the pressure sensing device 10B, such as memory 210.

In various examples, IMD 15B is configured to continue to monitor the input parameter during the entirety of time period while the pressure measurements are being taken. In some examples, if the status of the input parameters does not remain at the same levels and/or statuses that were initially required to trigger the trigger output signal, IMD 15B will discard all of the data associated with the pressure measurements taken during time period associated with issuance of the most recent trigger output signal. In other examples, once the trigger output signal has been transmitted, IMD 15B will receive and retain the data corresponding to the pressure measurement taking during time period, regardless of any changes to the status(es) on the input parameters used to initially trigger the pressure sensing. In such examples, the data collected from monitoring the input parameters during the time period while the pressure measurements are being taken will be saved and provided along with and as data corresponding to the pressure sensor measurements regardless of whether or not the status of the input parameters remains at the same levels and/or status that were initially required to trigger the trigger output signal.

Either during or at the conclusion of the time window, pressure sensing device 10B begins transmitting data corresponding to the sensed pulmonary artery pressures (block 408). The transmitted data is received by IMD 15B. In some examples, the transmitted data is transmitted to one or more external devices directly, such as external device 14B, or transceiver 24B. IMD 15B may further process the received data, and/or stores the received data in memory, such as memory 170. At some later time, the stored data may be retrieved and transmitted by wireless combination link, via communication circuitry 168. The data may be transmitted to an external device, such as external device 14B or transceiver 24B, and formatted for display by the external device. Transmission of data may include transmission of data collected by monitoring the input parameters during the entirety of time period while the pressure measurements were also being taken.

After completion of sensing the pulmonary blood pressure measurements for the period of the time window, and after completing transmission of the data corresponding to the sensed pulmonary blood pressures, pressure sensing device 10B transitions from the sensing mode back to the low-power mode (block 410). Pressure sensing device 10B may remain in the low-power mode until pressure sensing device 10B again receive a trigger output signal.

Figure 14:
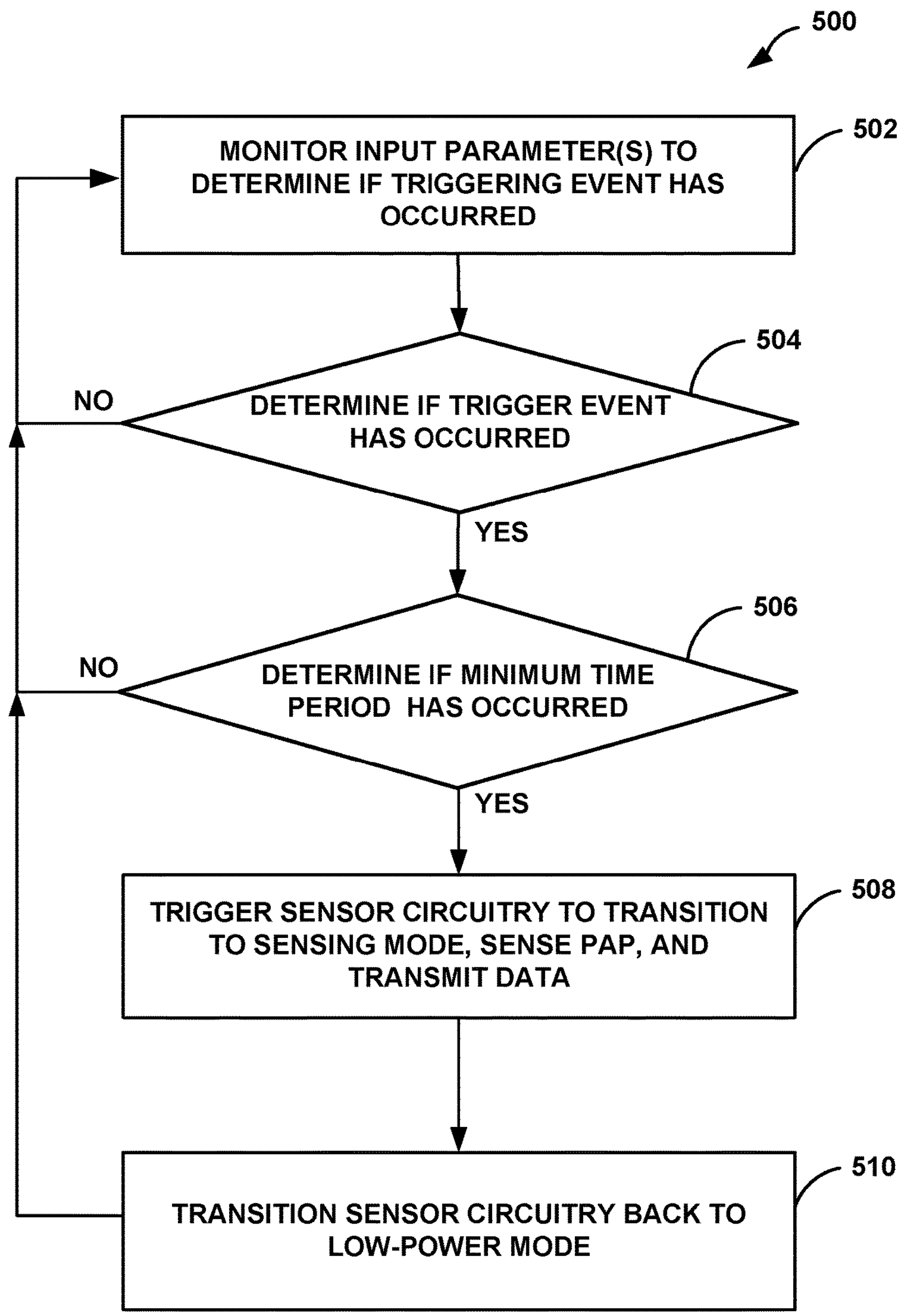
FIG. 14 illustrates a flowchart of another method according to various examples described in this disclosure.

FIG. 14 illustrates a flowchart of a method 500 according to various examples described in this disclosure. Although method 500 is described as being performed by IMD 15B and pressure sensing device 10B as illustrated and described with respect to FIG. 1B, method 500 is not limited to being performed by any particular device or devices, and may be performed by any device or devices configured to perform the functions of method 400, including devices and systems as otherwise described herein. According to method 500, IMD 15B monitors various input parameters, and determines that a triggering event has occurred based on current values, statuses, or some other derived parameter(s) based on monitoring the input parameters (block 502). In various examples, IMD 15B determines, using trigger circuitry 330, that a triggering event has occurred when the status of the input parameters, when logically ANDed together, results in a positive output based on the ANDed inputs (block 504). In various examples, the input parameters include a status associated with a patient's activity count, a patient's heart-rate, and a patient's respiratory rate. In various examples, trigger circuitry 330 receives additional information, such as the status of an enable/disable register in a memory 170, as an additional input parameter that is logically ANDed to determine if a triggering event has occurred.

If IMD 15B determines that a trigger event has not occurred, IMD 15B return to monitoring the input parameters as described above for block 502. Once a determination has been made at block 504 that a triggering event has occurred, IMD 15B determines if a minimum time period has occurred since the last trigger event had occurred (block 506). In some examples, the output of trigger circuitry 330 is logically ANDed with the output of at timer, the output of the timer providing a positive status only if the minimum time period has elapsed since the last trigger event occurred and a trigger output signal was transmitted to pressure sensing device 10B. If the minimum time period has not elapsed, IMD 15B returns to monitoring the input parameters (block 502). If the minimum time period has elapsed at block 506, IMD 15B proceeds to trigger pressure sensing device 10B to transition from the low power mode to a sensing mode in order to sense pressure measurements of a patient's pulmonary blood pressure, using for example sensor components 42 of the sensor circuit 12A (block 508). In some examples, sensing the patient's pulmonary blood pressure comprises sensing the pressures over a predetermined time window. Pressure sensing device 10B transmits the data corresponding to the pressure measurements back to IMD 15B (block 508). After completion of sensing the pulmonary blood pressure measurements for the period of the time window, and after completing transmission of the data corresponding to the sensed pulmonary blood pressures, pressure sensing device 10B transitions from the sensing mode back to the low-power mode (block 510). Pressure sensing device 10B may remain in the low-power mode until pressure sensing device 10B again receive a trigger output signal.

In various examples, IMD 15B is configured to continue to monitor the input parameter during the entirety of time period while the pressure measurements are being taken. IMD 15B in some examples discards the pressure measurements taken that are associated which the most recent trigger output signal if the same levels and/or statuses that were initially required to trigger the trigger output signal are not maintained during the time period over which the pressure sensor measurements were taken. Transmission of data may include transmission of data collected by monitoring the input parameters during the entirety of time period while the pressure measurements were also being taken.

Figure 15:
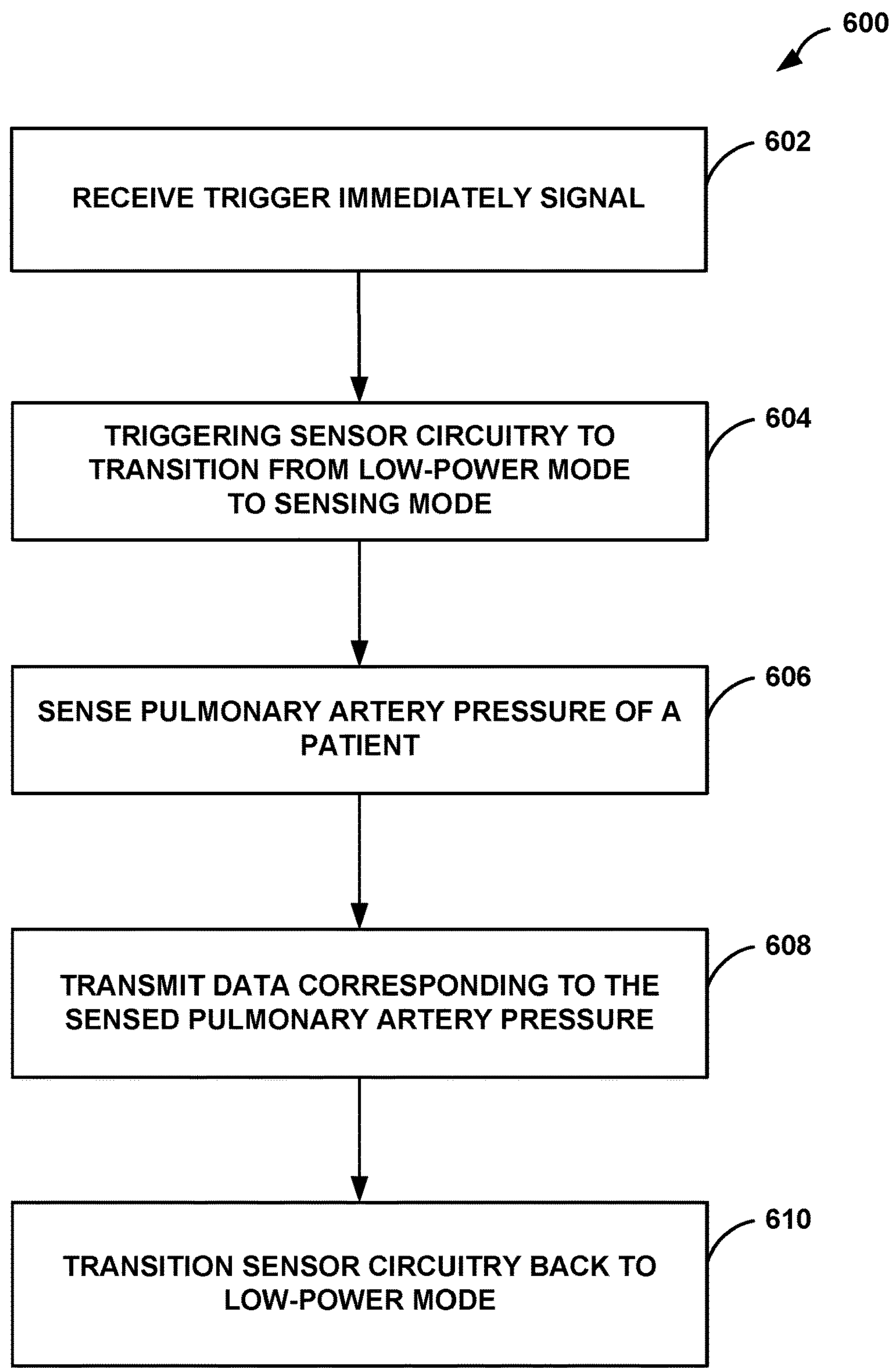
FIG. 15 illustrates a flowchart of another method according to various examples described in this disclosure.

FIG. 15 illustrates a flowchart of a method 600 according to various examples described in this disclosure. Although method 600 is described as being performed by IMD 15B and pressure sensing device 10B as illustrated and described with respect to FIG. 1B, method 600 is not limited to being performed by any particular device or devices, and may be performed by any device or devices configured to perform the functions of method 600, including devices and systems as otherwise described herein. According to method 600, IMD 15B may be monitoring various input parameters, and while monitoring input parameters, receives a trigger immediately signal (block 602). In various examples, the trigger immediately signal is transmitted from an external device, such as external device 14B, and is received by communication circuitry 168 of IMD 15B.

In response to receiving the trigger immediately signal, IMB 15B triggers pressure sensing device 10B to transition from a low-power mode to a sensing mode (block 604). In various examples, IMD 15B, using trigger circuitry 330, provides a trigger output signal to pressure sensing device 10B indicating that a triggering event has occurred regardless of the status of the input parameters being monitored by IMB 15B for input parameter statuses, the output of the logical AND function monitoring the input parameter statuses logically ORed to an input having a status based on receiving or not receiving a trigger immediately signal. The logical OR function of trigger circuitry 330 provides a trigger output signal if the ANDed inputs from the input parameters provided to trigger circuitry 330 all provide a positive output, or the status line indication whether a trigger immediately signal has or has not been received at IMB 15B. In this manner, the receipt of a trigger immediately signal will cause trigger circuitry 330 to output a trigger output signal regardless of the statute of the input parameters being monitored by the trigger circuitry 330. IMD 15B, in response to receiving the trigger immediately signal, generates the trigger output signal, and wirelessly transmits the trigger output signal to pressure sensing device 10B.

Once pressure sensing device 10B has received the trigger output signal, pressure sensing device 10B transitions from the low-power mode to a sensing mode, and begins sensing pulmonary blood pressure measurements, using for example sensor components 42 of the sensor circuit 12B (block 606). In various examples, pressure sensing device 10B is configured to take pulmonary blood pressure measurements, either continuously or at some predefined sample rate, for a period of defined by a time window having a predefined length of time. In various examples, the predefined sample rate is 64 Hz (sample measurement taken approximately every 15.6 milliseconds), and the length to the time window is defined to have a length of twenty seconds. However, other sample rates and/or lengths for the time window are contemplated by various examples described in this disclosure. Other sample rates may include rates having values lower or higher than 64 Hz. For example, other sample rates may include a sample rate of 128 Hz, or another sample rates may include a sample rate of 256 Hz. In various examples, the sensed pulmonary blood pressure measurements may be processed by processing circuitry included in pressure sensing device 10B, such as processing circuitry 200, and stored in a memory on-board the pressure sensing device 10B, such as memory 210.

Either during or at the conclusion of the time period defined by the time window, pressure sensing device 10B begins transmitting data corresponding to the sensed pulmonary artery pressures (block 608). The transmitted data is received by IMD 15B. In some examples, the transmitted data is transmitted to one or more external devices directly, such as external device 14B, or transceiver 24B. IMD 15B may further process the received data, and/or store the received data in memory, such as memory 170. At some later time, the stored data may be retrieved and transmitted by wireless combination link, via communication circuitry 168. The data may be transmitted to an external device, such as external device 14B or transceiver 24B, and formatted for display by the external device.

After completion of sensing the pulmonary blood pressure measurements for the period of the time window, and after completing transmission of the data corresponding to the sensed pulmonary blood pressures, pressure sensing device 10B transitions from the sensing mode back to the low-power mode (block 610). Pressure sensing device 10B may remain in the low-power mode until pressure sensing device 10B again receive a trigger output signal. In various examples, IMD 15B is configured to continue to monitor the input parameter during the entirety of time period while the pressure measurements are being taken. IMD 15B in some examples discards the pressure measurements taken that are associated which the most recent trigger output signal if the same levels and/or statuses that were initially required to trigger the trigger output signal are not maintained during the time period over which the pressure sensor measurements were taken. Transmission of data may include transmission of data collected by monitoring the input parameters during the entirety of time period while the pressure measurements were also being taken.

The techniques of this disclosure may be implemented in a wide variety of computing devices, medical devices, or any combination thereof. Any of the described units, modules or components may be implemented together or separately as discrete but interoperable logic devices. Depiction of different features as modules, units, circuits, or circuitry, is intended to highlight different functional aspects and does not necessarily imply that such modules, units, circuits, or circuitry must be realized by separate hardware or software components. Rather, functionality associated with one or more modules, units, circuits, or circuitry may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A method comprising:

determining, by processing circuitry of an implantable medical device implanted in a patient, that a triggering event has occurred based on statuses for a set of physiological parameters associated with the patient, the physiological parameters indicative of the patient engaging in a patient initiated physical activity;

generating, by trigger circuitry of the implantable medical device, a trigger output signal in response to the determination that the triggering event has occurred;

wirelessly transmitting, by a communication circuitry of the implantable medical device, the trigger output signal to a pressure sensing device implanted in a vessel of the patient;

triggering, based on receiving the trigger output signal at a communication circuitry of the pressure sensing device, the pressure sensing device to sense a cardiovascular pressure of the patient; and transmitting, by the communication circuitry of the pressure sensing device, a wireless signal to the implantable medical device, the wireless signal comprising data corresponding to the sensed cardiovascular pressure of the patient; and wherein determining that the triggering event has occurred based on at least one status for the set of physiological parameters associated with the patient further comprises:

determining, by a timer in the implantable medical device, if a minimum amount of time has elapsed since a last triggering event has occurred, and generating a trigger output signal only if the minimum amount of time has elapsed and only then in response to the determination that the triggering event has occurred based on the statuses for the set of physiological parameters associated with the patient.

2. The method of claim 1, wherein determining that the triggering event has occurred comprises:

monitoring, by a processing circuitry of the implantable medical device, a value for each of the set of physiological parameters associated with the patient to determine a current value for each of the set of physiological parameters;

comparing, by the processing circuitry of the implantable medical device, each of the current values of the set of physiological parameters to a threshold value for that physiological parameter to determine a status for each of the physiological parameters, and automatically determining, by the trigger circuitry, that the triggering event has occurred if each of the determined statuses for the set of physiological parameters indicates that the current value for each of the physiological parameters satisfies the threshold value defined for that physiological parameter.

3. The method of claim 2, wherein the monitored physiological parameters comprise at least one of a measurement of an activity count for the patient, a measurement of a heart rate for the patient, and a measurement of a respiration rate of the patient.

4. The method of claim 2, wherein generating the trigger output signal in response to the determination that the triggering event has occurred comprises:

performing, by the trigger circuitry, a logical AND function of the statuses for each of the physiological parameters; and a providing a status of an output of the logical AND function as an output from the trigger circuitry.

5. The method of claim 1, wherein triggering the pressure sensing device to sense a cardiovascular pressure of the patient comprises triggering the pressure sensing device to sense a pulmonary artery pressure of the patient.

6. The method of claim 1, wherein triggering the pressure sensing device to sense the cardiovascular pressure of the patient comprises sensing the cardiovascular pressure of the patient over a predetermined window of time.

7. The method of claim 6, wherein sensing the cardiovascular pressure of the patient comprises sensing a plurality of pressure values of a pulmonary artery pressure of the patient at a predefined sampling rate over a time period of the predetermined window of time.

8. The method of claim 1, wherein triggering the pressure sensing device to sense the cardiovascular pressure of the patient further comprises:

triggering the pressure sensing device to transition from a low-power mode to a sensing mode; and sensing, by the pressure sensing device, the cardiovascular pressure of the patient while the pressure sensing device is in the sensing mode.

9. The method of claim 8, further comprising:

completing the sensing of the cardiovascular pressure of the patient over a predetermined window of time;

completing the transmission of the wireless signal sent from the pressure sensing device to the implantable medical device, and transitioning the pressure sensing circuitry from the sensing mode back to the low-power mode.

10. The method of claim 1, further comprising:

receiving, by the communication circuitry of the implanted medical device, a request signal transmitted to the implanted medical device from an external device;

initiating, by a timer, a predefined time period in response to receiving the request signal; and generating, by the trigger circuitry, the trigger output signal only if during the predefined time period the triggering event occurs based on the statuses for the set of physiological parameters associated with the patient being indicative that the patient is engaging in a patient initiated physical activity.

11. The method of claim 1, further comprising:

receiving, by the communication circuitry of the implantable medical device, a request signal transmitted to the implantable medical device from an external device; and generating, by the trigger circuitry, the trigger output signal regardless of the statuses of the set of physiological parameters.

12. The method of claim 1, wherein sensing the cardiovascular pressure of the patient further comprises determining, by the processing circuitry of the implantable medical device, at least one of a systolic pressure value, a diastolic pressure value, and a mean value for each cycle of the cardiovascular pressures associated with a heartbeat of the patient.

13. An implantable medical device, comprising:

processing circuitry configured to receive input signals from one or more sensors, the input signals comprising signals generated in response to measured physiological parameters associated with a patient, and to determine a status for each of a set of input parameters based on the measured physiological parameters, the status for each of the set of input parameters indicative of whether or not current value for the input parameter satisfies a threshold value for that input parameter;

trigger circuitry configured to automatically generate a trigger output signal based at least in part on a determination that the statuses of the input parameters are indicative of the patient engaging in a patient initiated physical activity;

communication circuitry configured to receive the trigger output signal generated by the trigger circuitry, and to wirelessly transmit the trigger output signal to a pressure sensing device that is adapted to be implanted in a vessel of the cardiovascular system of the patient, the pressure sensing device configured to sense a cardiovascular pressure upon receipt of the trigger output signal; and a timer, the timer configured to provide a status indication that is indicative of whether a minimum time period has elapsed since the last occurrence of the trigger circuitry issuing a trigger output signal;

the trigger circuitry configured to receive that status indication provided by the timer, and to only issue a trigger output signal if the status indication indicates that the minimum time period has elapsed since the last issuance of a trigger output signal.

14. The implantable medical device of claim 13, wherein the determination of a status for each of a set of input parameters based on the measured physiological parameters comprises the processing circuitry configured to:

monitor input signals provided by the one or more sensor circuits to determine a current value for each of the set of input parameters based the monitored input signals;

compare each of the current values of the set of input parameters to at least one threshold value defined for that input parameter to determine if the current value for each input parameter satisfies the at least one threshold value defined for that input parameter.

15. The implantable medical device of claim 13, wherein at least one of the input signals received from the one or more sensors includes an accelerometer output signal generated by an accelerometer included within the implantable medical device, the processing circuitry configured to receive the accelerometer output signal from the accelerometer and to generate a current value for an activity count of the patient indicative of whether a patient has taken a step based at least in part on the accelerometer output signal.

16. The implantable medical device of claim 13, wherein the trigger circuitry comprises a logic circuit configured to logically AND the statuses of the set of input parameters, and to automatically generate the trigger output signal if all the statuses of input parameters are indicative of a positive status.

17. The implantable medical device of claim 13, wherein the communication circuitry is configured to receive an "immediate" request signal transmitted from an external device;

the trigger circuitry configured to receive the "immediate" request signal from the communication circuitry, to initiate a timer to time a predefined time period in response to receiving the "immediate" request signal, and to generate the trigger output signal only if during the predefined time period the triggering event has occurred based on the statuses for the set of physiological parameters associated with the patient being indicative that the patient is engaging in some form of patient initiated physical activity.

18. The implantable medical device of claim 13, wherein the communication circuitry is configured to receive an "immediate" request signal transmitted from an external device;

the trigger circuitry configured to receive the "immediate" request signal from the communication circuitry, and to generate the trigger output signal regardless of the statuses for the set of physiological parameters associated with the patient being indicative that the patient is engaging in some form of patient initiated physical activity.

19. The implantable medical device of claim 13, further comprising:

a housing adapted to be implanted at a position outside of a heart of the patient, the housing including sensor circuitry coupled to a plurality of electrodes located on an outer surface of the housing, the sensor circuitry and the plurality of electrodes configured sense an EGM signal generated by the heart of the patient.

20. The implantable medical device of claim 13, further comprising:

a housing adapted to be implanted outside a heart of the patient, the housing including sensing circuitry coupled to at least one lead including one or more electrodes adapted to be placed in electrical contact with selected portions of the cardiac anatomy of the patient and configured to sense an cardiac EGM signal generated by the heart of the patient, the housing further comprising a therapy delivery circuitry coupled to the one or more electrodes, the therapy delivery circuitry configured to provide electrical stimulation to the electrodes to deliver at least one of pacing or defibrillation to the patient based at least in part on the sensed EGM signal.

21. The implantable medical device of claim 13, wherein the pressure sensing device is adapted to be implanted in the pulmonary artery of the patient and is configured to sense a pulmonary artery pressure of the patient upon receiving the trigger output signal.

* * * * *